United States Patent
Skov et al.

(10) Patent No.: US 11,739,194 B2
(45) Date of Patent: Aug. 29, 2023

(54) GLYCEROL-SILICONE ELASTOMERS AS ACTIVE MATRICES WITH CONTROLLABLE RELEASE PROFILES

(71) Applicant: Danmarks Tekniske Universitet, Kgs. Lyngby (DK)

(72) Inventors: Anne Ladegaard Skov, Frederiksberg (DK); Michael Adrian Brook, Ancaster (CA); Piotr Stanislaw Mazurek, Virum (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 196 days.

(21) Appl. No.: 16/758,813

(22) PCT Filed: Nov. 23, 2018

(86) PCT No.: PCT/EP2018/082388
§ 371 (c)(1),
(2) Date: Apr. 23, 2020

(87) PCT Pub. No.: WO2019/101932
PCT Pub. Date: May 31, 2019

(65) Prior Publication Data
US 2021/0179808 A1    Jun. 17, 2021

(30) Foreign Application Priority Data

Nov. 23, 2017  (EP) .................................... 17203261
Jun. 7, 2018   (EP) ...................................... 8176569

(51) Int. Cl.
| | | |
|---|---|---|
| A61K 47/10 | (2017.01) | |
| C08K 5/053 | (2006.01) | |
| A61K 31/05 | (2006.01) | |
| A61K 47/34 | (2017.01) | |
| C08J 3/205 | (2006.01) | |
| C08K 5/1545 | (2006.01) | |

(52) U.S. Cl.
CPC ............. C08K 5/053 (2013.01); A61K 31/05 (2013.01); A61K 47/10 (2013.01); A61K 47/34 (2013.01); C08J 3/2053 (2013.01); C08K 5/1545 (2013.01); C08J 2383/04 (2013.01)

(58) Field of Classification Search
CPC ........ C08K 5/053; C08K 5/1545; C08K 5/13; C08K 5/0008; A61K 31/05; A61K 47/10; A61K 47/34; A61K 9/0014; A61K 9/7007; C08J 3/2053; C08J 2383/04; C08L 83/04

See application file for complete search history.

(56) References Cited

U.S. PATENT DOCUMENTS

| | | |
|---|---|---|
| 5,028,430 A | 7/1991 | Sanders et al. |
| 2001/0016609 A1 | 8/2001 | Meguriya et al. |
| 2003/0180281 A1 | 9/2003 | Bott et al. |
| 2007/0218115 A1 | 9/2007 | Bott et al. |
| 2009/0036304 A1* | 2/2009 | Misner .................. C09D 11/50 503/201 |
| 2010/0075056 A1 | 3/2010 | Axisa et al. |

FOREIGN PATENT DOCUMENTS

| | | |
|---|---|---|
| JP | S62-174031 | 7/1987 |
| JP | 2001-220510 A | 8/2001 |
| JP | 2005-528425 | 9/2005 |
| WO | WO 2016/066734 A1 | 5/2016 |
| WO | WO 2016/189117 A1 | 12/2016 |

OTHER PUBLICATIONS

Hajek, M.; Skopal, F. Treatment of glycerol phase formed by biodiesel production. Bioresource Technology. vol. 101, 9, 3242-3245. (Year: 2010).*
Mazurek, P. et al., "Green silicone elastomer obtained from a counterintuitively stable mixture of glycerol and PDMS" Polymer, Jan. 2016, pp. 1-7, vol. 87.
International Search Report for PCT/EP2018/082388 dated Apr. 10, 2019.
Mazurek, P. et al., "Glycerol as high-permittivity liquid filler in dielectric silicone elastomers" J.Appl.Polym Sci, Apr. 2016, pp. 44153-44161, vol. 113.
Mazurek, P. et al., "Glycerol-silicone elastomers as active matrices with controllable release profiles" Langmuir, Aug. 2018, pp. 11559-11566, vol. 34(38).
Office Action received in JP Patent Application No. 2020-522943, dated Nov. 1, 2022.

* cited by examiner

*Primary Examiner* — Jessica Worsham
(74) *Attorney, Agent, or Firm* — Knobbe Martens Olson & Bear LLP

(57) ABSTRACT

Herein is disclosed an elastomeric silicone composition comprising at least a first and a second glycerol phase which are distinct from each other and a method of making the same. The elastomeric compositions are special therein that zero-order active substance release can reversibly be obtained by modifying the glycerol content of the silicone composition.

4 Claims, 16 Drawing Sheets

| Sample name [a] | Glycerol content [phr] | Type and amount of active substance in glycerol | Mixing ratio of silicone(base: curing agent) | Composite morphology [b] |
|---|---|---|---|---|
| S184 | - | - | 10:1 | n/a |
| G40_S184 | 40 | - | 10:1 | discrete |
| G80_S184 | 80 | - | 10:1 | discrete |
| G120_S184 | 120 | - | 10:1 | bicontinuous |
| S184_20:1 | - | - | 20:1 | n/a |
| G40_S184_20:1 | 40 | - | 20:1 | discrete |
| G80_S184_20:1 | 80 | - | 20:1 | discrete |
| G40_HQ5_S184 | 40 | HQ, 5 wt.% | 10:1 | discrete |
| G80_HQ5_S184 | 80 | HQ, 5 wt.% | 10:1 | discrete |
| G120_HQ5_S184 | 120 | HQ, 5 wt.% | 10:1 | bicontinuous |
| G80_HQ5_S184_2000rpm [c] | 80 | HQ, 5 wt.% | 10:1 | discrete |
| G80_HQ5_S184_20:1 | 80 | HQ, 5 wt.% | 20:1 | discrete | a   Additional information on sample thickness is added at the end of each sample name when necessary
b   Composite morphology differentiates between discrete (separate glycerol domains) and bicontinuous maxi-morphologies [18]
c   Composition mixed at 2000 rpm Table 1

Fig. 15

| Silicone | Produced by | Curing system | Max glycerol [phr] | Comments |
|---|---|---|---|---|
| Sylgard 184 | Dow Corning | Hydrosilylation | 160 | More with Surfactants |
| Sylgard 184 + 10 phr Krytox, | Dow Corning/ DuPont | Hydrosilylation | 70 | |
| Powersil XLR630 | Wacker Chemie | Hydrosilylation | 40 | |
| Powersil XLR630 with solvents | Wacker Chemie | Hydrosilylation | 120 | |
| Elastosil P7684/40 | Wacker Chemie | Hydrosilylation | 60 | |
| Elastosil RT620 | Wacker Chemie | Hydrosilylation | 80 | Not stable without silica |
| MG7-9900 adhesive | Dow Corning | Hydrosilylation | 60 | No silica |
| MG7-9850 adhesive | Dow Corning | Hydrosilylation | 60 | No silica |
| Elastosil RTK | Wacker Chemie | Condensation | 120 | Not perfectly stable |
| Elastosil RT563 | Wacker Chemie | Condensation | 20 | Much more with surfactants |

* Krytox –vinyl terminated perfluoroether allylamide from DuPont

Table 2

Fig. 16

GLYCEROL-SILICONE ELASTOMERS AS ACTIVE MATRICES WITH CONTROLLABLE RELEASE PROFILES

CROSS REFERENCE TO RELATED APPLICATIONS

This application is a U.S. National Phase Application of PCT International Application Number PCT/EP2018/082388, filed on Nov. 23, 2018, designating the United States of America and published in the English language, which is an International Application of and claims the benefit of priority to European Patent Application No. 17203261.7, filed on Nov. 23, 2017, and European Patent Application No. 18176569.4, filed on Jun. 7, 2018. The disclosures of the above-referenced applications are hereby expressly incorporated by reference in their entireties.

TECHNICAL FIELD

In the field of active matrices for controlled active substance release there are described silicone elastomers comprising glycerol as active matrices with controlled release profiles.

BACKGROUND

Active substance release regimes, in particular drug regimes, must be controlled for optimal effect, in particular for optimal therapeutic effect, of the released active substance. While it is relatively straightforward to create first order release matrices, it can be challenging to avoid an initial burst. Matrices with zero-order profiles are perceived to be beneficial in many cases, but are even more difficult to formulate.

In the present disclosure there is described a simple synthesis of elastomeric composites prepared from silicone in which the active substance is dispersed in glycerol. The release of glycerol-soluble excipients from films of these materials was surprisingly found to be tunable with respect to the order of release (zero- or first-order) simply by changing the glycerol content. Importantly, release from the elastomers showed no burst effect. The discrete glycerol domains embedded within a silicone matrix act as reservoirs for releasable substances, preferably releasable active substances. In some embodiments, the releasable active substance is a drug.

For the elastomers of the present invention, it was surprisingly found that the active substances are released from the elastomer matrices, upon contact with aqueous media, exhibiting zero-order, near zero-order or first-order release kinetics under controllable conditions. The present inventors identified various parameters showing an influence on the release process including glycerol content, glycerol domain size (globule diameter or morphology) and/or membrane thickness. By elucidating and developing guidelines for creating matrices capable of delivering active substances at desired rates, the inventors have been able to create matrices comprising at least one active substance, i.e. a drug, to be delivered, but also two, three or more, with tunable control-parameters.

A surprising benefit of the present elastomeric active substance delivery matrices is that the composites proved to absorb significant amounts of liquid water (up to 1850% of sample mass), a feature that can be tuned by manipulation of the composite structure. In topical active substance delivery, in particular in topical drug delivery, using elastomer patches comprising at least one active substance, this is highly appreciated as it can help prevent or alleviate the discomfort of carrying a drug patch on a patient's skin due to the inability to transport moisture away from the skin; an effect which may also cause adhesive failure of the active substance delivery patch as well.

Increasingly, active substance regimes require precise modes of delivery over time; the paradigm of one pill every four hours is frequently not ideal.[1] In the most simple polymer-based active substance delivery systems, active substances are uniformly dispersed within a polymer in a form of a blend.[2] Such systems typically exhibit first-order release behavior as a consequence of Fickian transport.[3] This implies that active substances are released relatively rapidly initially (burst effect), but subsequently the release significantly decelerates.[4]

A wide variety of sophisticated systems based on different polymers has been designed to modify the release profiles. A particularly challenging delivery mode is zero-order, in which the release rate of the delivered active substance is independent of time and/or residual concentration in the delivery vehicle.[2] In general, zero-order release systems are technologically more difficult to create and therefore result in significantly higher prices.[5]

In previous works, the inventors have described a two-phase glycerol-silicone hybrid elastomer that, depending on formulation, possesses a bicontinuous or closed cell foam structure, cf. e.g. WO 2016/066734 A1 and WO 2016/189117 A1, which are herein incorporated by reference. Both constituents (glycerol and silicone) are understood to be biocompatible and non-toxic in many applications in the biomedical industry.[11-14] For example, silicone-coated wound dressings are well accepted because the silicone, which is highly permeable to oxygen that is needed for healing, does not adhere strongly or fixedly to the granulating wound, while providing an excellent seal that prevents bacterial ingress.[15-17]

The glycerol-silicone composites described in the prior art are created simply by providing high shear forces to virtually immiscible mixtures of glycerol and silicone prepolymer.[18] In this way stable glycerol-in-silicone emulsions are formed which, upon cross-linking of the silicone phase, form free-standing two-phase elastomeric composites.

Sophisticated examples of spherical drug vehicles like porous microspheres or polymer micelles have both proven to be capable of ensuring zero- or near zero-release behavior.[6,7] Furthermore, various types of gels and matrices have been employed to prepare drug delivery membranes enabling first-order drug release lasting from few hours up to few weeks and possibly even months.[8-10] Numerous approaches utilize two or more distinct release mechanisms which, upon proper adjustment, result in zero-order release.[3,4] However, these are neither readily prepared nor manipulated.

Commercial drug delivery technologies developed so far share some common features. Firstly, all drug delivery systems must be biocompatible and non-toxic. Secondly, the technologies should be simple enough to allow for creating cost-efficient products. The inventors have reasoned that an open foam structure could be tailored to give zero-order release, particularly in a topical application, for example wound dressings, where surface area is more important than depth of the device.

The present inventors have now surprisingly realized that the glycerol-silicone elastomeric matrices developed by the inventors are easily tunable matrices for active substance delivery, in particular for drug delivery, which have led the inventors to formulate the below invention and aspects and embodiments thereof.

In accordance with the prior art (WO 2016/189117 A1) elastomeric, single or multiple excipient glycerol-silicone matrices can be prepared as described below.

In particular, in accordance with the prior art, an elastomeric composition can be prepared, the composition comprising a silicone elastomer, glycerol, at least one crosslinking agent, and optionally one or more excipients comprised in the glycerol, and wherein the glycerol composition is present as discrete droplets in the silicone elastomer, and wherein the discrete droplets of glycerol are obtained through the application of shear at a level of about from 1000 rpm to about 5000 rpm of a mixture of a silicone elastomer, glycerol, at least one crosslinking agent and optionally one or more excipients.

Following the method of the prior art results in elastomeric matrices, wherein, when two or more excipients are present, all the excipients are evenly distributed in the single, glycerol composition or phase.

Herein we describe for the first time methods to obtain elastomeric matrices comprising at least two, but preferably multiple glycerol phases and compositions. The glycerol phases can individually comprise one or more excipients and/or active substances, e.g. drugs, including, but not limited to aides to active substance delivery. Due to the stability of the glycerol phases, which can be present in unmixed states, the excipients will be compartmentalized and prevented from mixing before use of the elastomeric matrices for active substance delivery. Elements of the present invention have, subsequent to the filing of the present priority applications, been filed by the inventors[25] with, and published on Aug. 29, 2018 by, ACS Journal Langmuir, Langmuir 2018, 34, 11559-11566: *Glycerol-Silicone Elastomers as Active Matrices with Controllable Release Profiles*, which is herein incorporated by reference.

By preparing elastomeric matrices with multiple glycerol phases and compositions, the usability of the matrices are increased as cross-interaction between excipients can be decreased or even eliminated. Further, dual-release, or multiple release active substance (e.g. drugs) delivery compositions can be prepared with excipients, which under normal conditions interact detrimentally to their intended target use.

In particular, and building on reports by the present inventors[18], upon contact with an aqueous phase the composite elastomers of the invention absorb significant quantities of water and at the same time release glycerol. Herein we report glycerol release experiments conducted over 24 hours showing that the percentage amount of released glycerol scales with the glycerol loading ranging from values close to 0% and 100%. Building on this discovery, the inventors herein propose that other substances incorporated into the glycerol domains could be released from the matrix in a similar way. That is, the glycerol compositions would act as reservoirs for active substances and the active substance delivery process, in particular drug delivery processes, would be triggered upon contact with water, including wound exudate and/or skin moisture including sweat.

Definitions

In the present context the term "silicone elastomer" refers to a polymer that includes any inert compound made up of repeating units of siloxane of the formula —RR'SiO—, wherein R and R' are identical or different hydrocarbon groups and wherein the term is used in accordance with its IUPAC definition as a polymer that displays rubber-like elasticity.

In the present context the term "polysiloxane" refers to a compound of the form [RR'SiO]n, wherein R and R' are identical or different hydrocarbon groups, and wherein n is the number of repeating units. The term "polysiloxane" also refers to a compound of the form [RR'SiO]n, which may be partly functionalized in the sense that some R, R' groups have been replaced by or substituted with substituent groups. Non-limiting examples of such substituent groups include Cl, CN, F, S, $NH_2$, OH, alkenyl, and alkynyl. In addition, silicone compounds or silicone prepolymers or additives used for crosslinking may include functional groups known in the art, including compounds comprising SiH, SiOR, Si-oxime, and Si-carboxylate functions.

In the present context the term "polydimethylsiloxane", abbreviated "PDMS", refers to a compound of the formula $CH_3[Si(CH_3)_2O]_nSi(CH_3)_3$, where n is the number of repeating units. The term "polydimethylsiloxane" encompasses derivatives thereof, wherein one or more methyl groups in PDMS is replaced by, e.g. SiH, hydroxy-, vinyl-, allyl-groups in a pendant or terminal position.

In the present context, the term "curing" refers to the process of cross-linking of polymer chains.

In the present context, the terms "crosslinker" and "crosslinking agent" are used interchangeably and refer to a chemical compound or compounds facilitating the crosslinking of polymer chains, in particular silicone polymer chains. No particular limitation on the actual composition of the crosslinker or crosslinking agent is to be inferred by the selected language or intended thereby. Examples of a crosslinker or a crosslinking agent may e.g. be a metal, a small molecule, a polymeric crosslinker or even a crosslinking composition comprising more than one active crosslinker or crosslinking agent involved in the crosslinking process.

In the present context, the term "phr" used for describing glycerol content in all compositions corresponds to glycerol weight amount per hundred weight parts of silicone elastomer.

In the present context, the term "thin film" refers to an elastomeric film having a typical thickness range of about from 0.01 mm to 100 mm, such as about from 0.05 mm to 10 mm, such as about 0.1 mm to 5 mm, such as about 0.5 mm to 2.5 mm, such as about 1 mm.

In the present context, the term excipient is used in the sense of an added substance to either a silicone phase or a glycerol phase of the invention. Hence, in the context of the present disclosure, an excipient is a substance comprised in the compositions of the invention additional to either glycerol or silicone. Excipients may e.g. be selected from the group consisting of active substances, in particular active substances for human or animal use, in particular drugs, and/or from catalysts, inhibitors, flow agents, silicone oils, solvents, fillers, blowing agents, reinforcing substances, and plasticizers. Other examples of excipients are given herein below.

In the context of the present invention, an active substance is a substance, which can be released from the compositions of the invention following a release rate of zero or higher orders as detailed herein. Particularly, active substances are intended to comprise such substances, which upon their release from the compositions of the invention are chemically and/or biologically active at a surface or in a human or an animal body, such as pharmacological active ingredients and/or drugs.

SUMMARY OF THE INVENTION

In a first aspect of the invention, there are disclosed elastomeric silicone compositions comprising at least a first and a second glycerol phase which are distinct from each other as detailed below. The phases may be individually continuous, yet distinct structures embedded in an elastomeric silicone matrix composition, but will normally be present as discrete globules or drops embedded in an elastomeric silicone matrix composition.

The inventors have surprisingly discovered, that such elastomeric compositions when cured to form a silicone elastomer matrix comprising at least two distinct glycerol phases, are highly suitable for active substance delivery patches, in particular for transdermal drug delivery patches, and that the active substance release kinetics from these compositions are easy to control and can reversibly be changed from first-order over near-zero-order to zero-order active substance release kinetics.

In the first aspect and embodiment of the invention there is disclosed an elastomeric silicone composition comprising at least a first and a second glycerol phase, which are distinct from each other therein that the at least a first and a second glycerol phases differ at least by the presence of a first excipient in the first glycerol phase, which is not present in the second glycerol phase.

In an embodiment of the elastomeric silicone composition there is disclosed: the at least a first and a second glycerol phases differ at least by the presence of a first drug and/or a first colorant in the first glycerol phase which is/are not present in the second glycerol phase.

In an embodiment of the elastomeric silicone composition there is disclosed: said a first excipient is selected from a first active substance, a first drug, a first colorant, or combinations thereof.

In an embodiment of the elastomeric silicone composition there is disclosed: the second glycerol phase comprises at least a second excipient, which is not present in the first glycerol phase.

In an embodiment of the elastomeric silicone composition there is disclosed: the second excipient is selected from a second active substance, a second drug, a second colorant, or combinations thereof.

In an embodiment of the elastomeric silicone composition there is disclosed: the first and the second excipients are respectively hydroquinone and erythrosine B.

In an embodiment of the elastomeric silicone composition there is disclosed: the elastomeric silicone composition is an elastomeric silicone composition prepared according to any of the methods of preparing an elastomeric silicone composition disclosed herein.

In an embodiment of the elastomeric silicone composition there is disclosed: the elastomeric silicone composition is an elastomeric silicone composition in the form of an emulsion or in the form of a cured elastomer. In one embodiment, the elastomeric silicone emulsion composition is in the form of a pre-cured emulsion composition.

In a second aspect of the invention there is disclosed a method of preparing an elastomeric silicone composition comprising at least two distinct glycerol phases comprising:
a) providing at least a first silicone composition comprising a first glycerol phase and a second silicone composition comprising a second glycerol phase;
b) mixing the at least a first and second silicone compositions at a shear level below from 1000 rpm; and
c) optionally, curing the mixed silicone composition obtained in b).

In an embodiment of the method of preparing an elastomeric silicone composition there is disclosed: the method wherein mixing in b) is continued until the at least first and second silicone compositions are fully blended in.

In an embodiment of the method of preparing an elastomeric silicone composition there is disclosed: the method wherein the shear level is below from 750 rpm, preferably below from 500 rpm.

In an embodiment of the method of preparing an elastomeric silicone composition there is disclosed: the method shear is applied for less than from 2 min, less than from 1 min, or less than from 0.5 min.

In an embodiment of the method of preparing an elastomeric silicone composition there is disclosed: the method wherein the first silicone composition is distinct from the second silicone composition by comprising at least a first excipient in the first glycerol phase of the first silicone composition which is not present in the second glycerol phase of the second silicone composition.

In an embodiment of the method of preparing an elastomeric silicone composition there is disclosed: the method wherein the at least a first excipient is selected from a first active substance, a first drug, a first colorant, or combinations thereof.

In an embodiment of the method of preparing an elastomeric silicone composition there is disclosed: the method wherein the second silicone composition comprises at least a second excipient in the second glycerol phase, which is not present in the first glycerol phase.

In an embodiment of the method of preparing an elastomeric silicone composition there is disclosed: the method wherein the at least a second excipient is selected from a second active substance, a second drug, a second colorant, or combinations thereof.

In an embodiment of the method of preparing an elastomeric silicone composition there is disclosed: the method wherein at least one of the at least a first silicone composition comprising a first glycerol phase and a second silicone composition comprising a second glycerol phase is obtained by:
i. providing a silicone pre-elastomer;
ii. providing glycerol;
iii. providing at least one crosslinking agent;
iv. providing one or more excipients and optionally one or more additives;
v. mixing the silicone pre-elastomer, the at least one crosslinking agent, the glycerol, and optionally one or more excipients and optionally one or more additives through the application of shear at a level of above from 1000 rpm to 5000 rpm.

In a third aspect according to the invention there is disclosed an active substance-release silicone elastomer composition having at least near-zero-order active substance release kinetics and comprising at least one distinct glycerol phase enclosed in a continuous silicone elastomer matrix, wherein an active substance to be released is comprised in the at least one distinct glycerol phase, and the at least one distinct glycerol phase is present to at least 60 phr in the silicone elastomer matrix.

In an embodiment of the active substance-release silicone elastomer composition having at least near-zero-order active substance release kinetics there is disclosed: the composition wherein the at least one distinct glycerol phase is present to between from 60 phr to 150 phr, from 70 phr to 140 phr, from 80 phr to 130 phr, from 90 phr to 120 phr, or from 100 phr to 110 phr in the silicone elastomer matrix.

In an embodiment of the active substance-release silicone elastomer composition having at least near-zero-order active substance release kinetics there is disclosed: the composition wherein when the at least one distinct glycerol phase is present in a concentration from 100 phr to 150 phr, preferably from 110 phr to 130 phr, and most preferably to a concentration of 120 phr in the silicone elastomer matrix, active substance release observing zero-order active substance release kinetics is obtained.

In an embodiment of the active substance-release silicone elastomer composition having at least near-zero-order active substance release kinetics there is disclosed: the composition wherein at least two distinct glycerol phases, each distinct glycerol phase comprising a respective active substance to be released, are enclosed in the continuous silicone elastomer matrix, with the proviso that the total concentration of glycerol in the silicone elastomer composition is present to between from 60 phr to 150 phr, to between from 70 phr to 140 phr, to between from 80 phr to 130 phr, to between from 90 phr to 120 phr, to between from 100 phr to 110 phr in the silicone elastomer matrix, preferably is present to between from 80 phr to 130 phr.

In an embodiment of the active substance-release silicone elastomer composition having at least near-zero-order active substance release kinetics there is disclosed: the composition wherein the silicone elastomer composition is a cured elastomeric silicone composition according to any of the embodiments disclosed herein.

In an embodiment of the active substance-release silicone elastomer composition having at least near-zero-order active substance release kinetics there is disclosed: the composition wherein a dimension of the active substance-release silicone elastomer composition is between from 0.1 mm to 5 mm.

In a fourth aspect of the invention there is disclosed a method of changing an active substance release kinetics reversibly between zero-order active substance release kinetics and first-order active substance release kinetics for an active substance-release silicone elastomer composition comprising at least one distinct glycerol phase enclosed in a continuous silicone elastomer matrix, wherein an active substance to be released is comprised in the at least one distinct glycerol phase, the method comprising adjusting the concentration of glycerol in an elastomeric silicone composition of a distinct glycerol phase comprising at least one active substance to be released from the glycerol phase above or below a first glycerol concentration threshold; speed-mixing the elastomeric silicone composition and distinct glycerol phase at between from 1000 rpm to 5000 rpm; and subsequently curing the resulting mixture.

In an embodiment of the method of changing an active substance release kinetics reversibly between zero-order active substance release kinetics and first-order active substance release kinetics for an active substance-release silicone elastomer composition there is disclosed: the method wherein the first glycerol concentration threshold is 60 phr glycerol total concentration of glycerol in the silicone elastomer composition.

In an embodiment of the method of changing an active substance release kinetics reversibly between zero-order active substance release kinetics and first-order active substance release kinetics for an active substance-release silicone elastomer composition there is disclosed: the method wherein the elastomeric silicone composition is an active substance-release silicone elastomer composition according to any of the embodiments disclosed herein.

In an embodiment of the method of changing an active substance release kinetics reversibly between zero-order active substance release kinetics and first-order active substance release kinetics for an active substance-release silicone elastomer composition there is disclosed: the method wherein an active substance release rate of an active substance comprised in a distinct glycerol phase comprised in the elastomeric silicone composition is adjusted by adjusting a cross-linking density during curing of the elastomeric silicone composition and/or is adjusted by changing a morphology of the resulting mixture of glycerol and elastomeric silicone composition.

BRIEF DESCRIPTION OF THE DRAWINGS

FIG. 15: Table 1—List of investigated samples with corresponding sample names.

FIG. 16: Table 2—Test of formation of compositions and of maximum glycerol loading.

DETAILED DESCRIPTION

Figure 1:
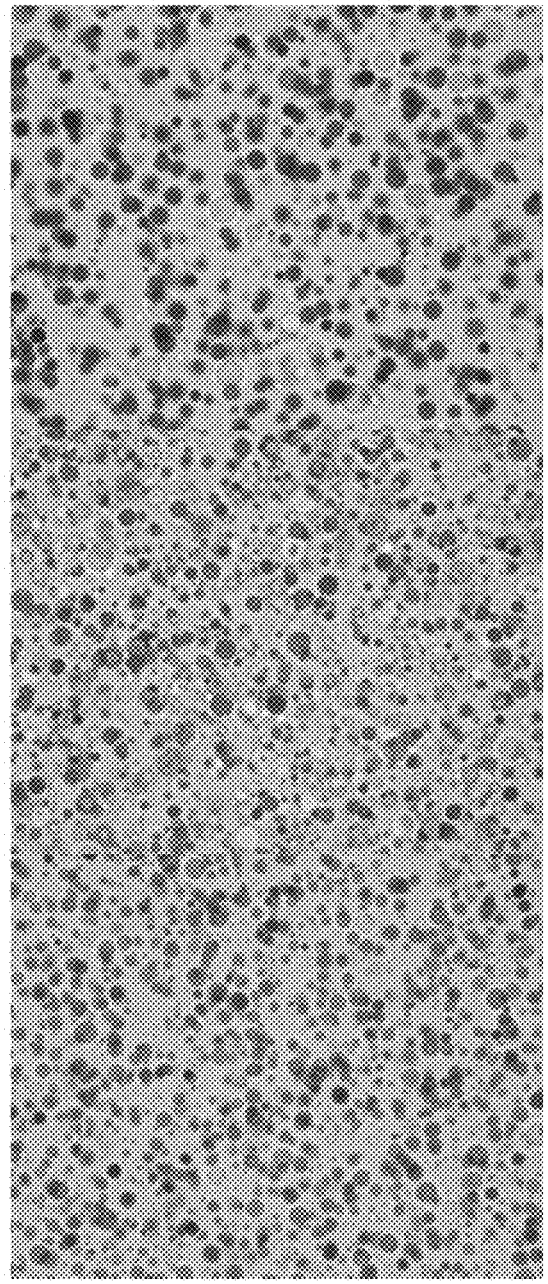
FIG. 1: Dual compartment silicone elastomer emulsion comprising two distinct glycerol phases with a respective red or blue colorant.

In an aspect, the present invention relates to a method of preparing an elastomeric silicone composition comprising at least two distinct glycerol phases comprising:
  a) providing at least a first silicone composition comprising a first glycerol phase and a second silicone composition comprising a second glycerol phase;
  b) mixing the at least a first and second silicone compositions at a shear level below from 1000 rpm; and c) optionally, curing the mixed silicone composition obtained in b).

The elastomeric silicone composition prepared according to the steps a) and b) will result in an emulsion which has been found to be unusually stable over long time (weeks). This is beneficial, as it will permit local production of cured elastomers of the elastomeric silicone composition from stock solution centrally provided, thereby permitting local adaptations of size and/or doses. Preferably, however, the elastomeric silicone composition of the invention is in the form of a cured elastomer as according to the above method and including step c).

It is a particular benefit of the present method that an elastomeric silicone composition comprising at least two distinct glycerol phases can be produced, wherein a first silicone composition is distinct from a second silicone composition by comprising at least a first excipient in the first glycerol phase of the first silicone composition which is not present in the second glycerol phase of the second silicone composition.

In some embodiments, and as illustrated herein, at least three distinct glycerol phases can be present in the cured elastomeric composition, and the present inventors have not observed anything hindering even further distinct glycerol phases, such as four distinct glycerol phases or higher. E.g. four distinct glycerol phases could be prepared by combining two elastomer silicone compositions comprising two distinct glycerol phases, and as would be understood by one skilled in the art, combining more than 2 excipient-in-glycerol phases may be present in the silicone by appropriate formulation of the procured materials.

Thereby excipients which otherwise cannot be combined and/or comprised in a silicone elastomer can be combined and/or comprised in the silicone elastomers of the present invention by compartmentalization, preferably by compartmentalization in different glycerol phases.

In some embodiments the at least a first excipient is a first active substance, a first drug or a first colorant or a combination thereof.

In other embodiments, also the second silicone composition comprises at least a second excipient in the second glycerol phase; which is not present in the first glycerol phase. In some embodiments, the at least a second excipient is a second active substance, a second drug, or a second colorant or a combination thereof.

In further embodiments, both the at least a first and the at least a second excipient are different active substances, such as erythrosine B and hydroquinone, and/or different colorants, such as a red dye and a blue dye.

It is a particular benefit of the invention that by compartmentalizing the active substances, a silicone elastomer can be prepared which may comprise a plurality of excipients which can be individually added to glycerol, such as e.g. one excipient added to a first volume of glycerol at a first temperature of dissolution and a second excipient added to a second volume of glycerol at a second temperature of dissolution, without the risk of cross-contamination nor, if e.g. one active substance is heat sensitive, e.g. a heat sensitive drug, risking active substance degradation during co-mixing with the other active substance, e.g. by non-heat sensitive drug enhancers. Following the present invention, each silicone composition can be prepared individually in separate production lines, and only combined prior to curing in c).

Figure 2:
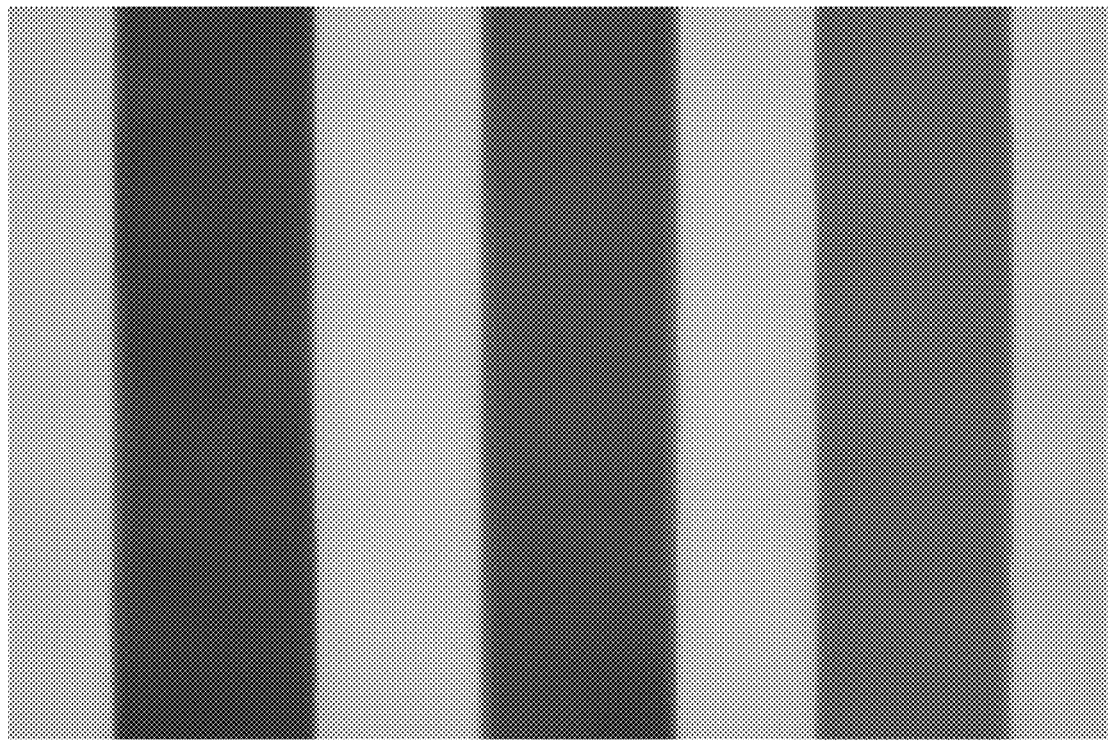
FIG. 2: Dual compartment cured silicone elastomer exhibiting a mixed color (purple).

In some embodiments, a respective colorant is added to a respective silicone composition. As illustrated in FIGS. 1 and 2, a combination color will result, which will provide simple, visual confirmation that mixing has been achieved and to which degree. If also different active substances are added to each respective glycerol phase, a user of the resulting cured elastomeric silicone composition, e.g. as a transdermal patch, will have visual confirmation under the microscope from the mixed color, that two glycerol phases are present in the cured elastomeric silicone composition, thereby enhancing patient safety.

In general, it is contemplated that mixing in b) is continued until the at least first and second silicone compositions are fully blended in. Preferably, the shear level is below from 750 rpm, preferably below from 500 rpm. In some embodiments shear is applied for less than from 2 min, less than from 1 min, or less than from 0.5 min.

In one aspect of the present invention there is further disclosed an elastomeric silicone composition comprising at least a first and a second glycerol phases which are distinct from each other.

In an embodiment thereof, the at least a first and a second glycerol phases differ at least by the presence of a first excipient in the first glycerol phase which is not present in the second glycerol phase.

In an embodiment thereof, the at least a first and a second glycerol phases differ at least by the presence of a first active substance, a first drug, and/or a first colorant in the first glycerol phase which is/are not present in the second glycerol phase.

In an embodiment thereof, the second glycerol phase comprises at least a second excipient, which is not present in the first glycerol phase. In an embodiment thereof, the second excipient is an active substance, preferably a releasable active substance. In preferred embodiments, the releasable active substance is a drug and/or a colorant.

In an embodiment thereof, the first and the second excipient are respectively hydroquinone and erythrosine B.

FIG. 1 details a dual compartment silicone elastomer comprising two distinct glycerol phases characterized therein that each glycerol phase is distinct by the presence of different excipients, the excipients being either a blue colorant (FIG. 1A) or a red colorant (FIG. 1B). FIG. 1C shows the elastomeric composition after mixing, wherein can be observed that the colorants remain separated in the glycerol globules and that hence the elastomer comprises two distinct glycerol phases. The images were recorded prior to curing.

FIG. 2 details the cured silicone elastomer (1 mm thickness) showing a blue band (left) a purple band (center) and a red band (right) proving homogenous mixing of the two colored phases prior to curing.

Figure 3:
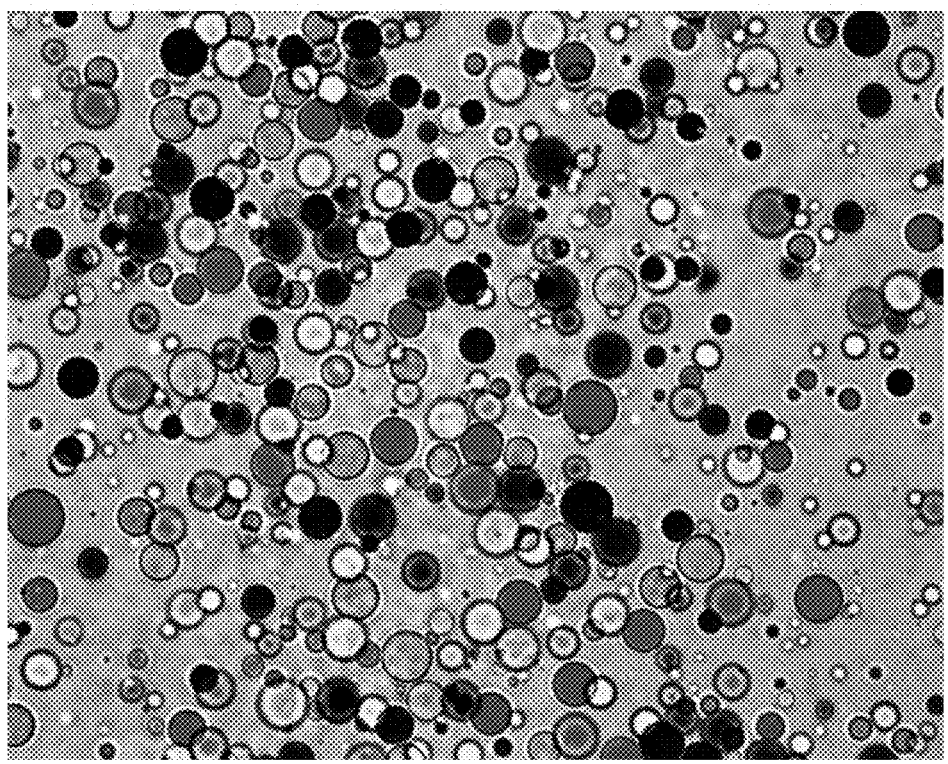
FIG. 3: Triple compartment silicone elastomer emulsion comprising three distinct glycerol phases with a respective red, blue, and green colorant.

FIG. 3 details a triple compartment silicone elastomer emulsion as a thin film under an optical microscope, prior to curing and comprising three distinct glycerol phases characterized therein that each glycerol phase is distinct by the presence of different excipients, the excipients being either a blue colorant, a red colorant, or a green colorant.

The yellow color represents an artefact from out-of-focus plane green light. Hence, yellow droplets are in fact green.

In some embodiments of the invention, the method of preparing an elastomeric silicone composition comprising at least two distinct glycerol phases comprises obtaining at least one of the at least a first silicone composition comprising a first glycerol phase and a second silicone composition comprising a second glycerol phase by:

i. providing a silicone pre-elastomer;
ii. providing glycerol;
iii. providing at least one crosslinking agent;
iv. providing one or more excipients and optionally one or more additives;

v. mixing the silicone pre-elastomer, the at least one crosslinking agent, the glycerol, and optionally one or more excipients and optionally one or more additives through the application of shear at a level of above from 1000 rpm to 5000 rpm.

Thereby, the preparation of at least one of the glycerolic phases can be in accordance with the prior art as described in WO 2016/189117 A1.

In accordance with the prior art, an elastomeric composition can be prepared from a composition comprising a silicone elastomer, glycerol, at least one crosslinking agent, and optionally one or more excipients, wherein the glycerol can be present as discrete droplets in the silicone elastomer, and wherein the discrete droplets of glycerol are obtained through the application of shear at a level of from about 1000 rpm to about 5000 rpm of a mixture of a silicone elastomer, glycerol, at least one crosslinking agent and optionally one or more excipients.

Following the method of the prior art results in an elastomeric silicone matrix comprising a single glycerolic phase. When two or more excipients are present in the prior art compositions, and both or all are dissolvable or miscible in glycerol, then all the excipients will be evenly distributed in the single, glycerol phase of the silicone elastomer matrices of the prior art. The compositions of the present invention do not suffer from these drawbacks, but rather may comprise at least two, and without difficulty multiple, glycerolic phases, which are distinct from each other e.g. being distinct by comprising each a different excipient or other further component.

According to the prior art and hence representing a method suitable for use with the present invention, there is comprised a method of preparing an elastomeric silicone composition comprising a single glycerol phase, which can be according to any one of the methods and items described in this section of the present disclosure, which method may comprise:

i. providing a silicone pre-elastomer;
ii. providing glycerol;
iii. providing at least one crosslinking agent;
iv. optionally providing one or more excipients and optionally one or more additives;
v. mixing the silicone pre-elastomer, the at least one crosslinking agent, the glycerol, and optionally one or more excipients and optionally one or more additives through the application of shear at a level of from about 1000 rpm to about 5000 rpm; and
vi. curing the mixture obtained in v.

As has been detailed herein above and below, the method of the present invention does not immediately employ curing step vi, but rather mixes at least two separate pre-elastomeric compositions comprising each a separate glycerol phase with separate excipients, and prepared according to steps i. to v. above before curing in step vi. However, the teachings and the embodiments relating to the individual elastomeric compositions as detailed in the prior art relating to steps i. to vi. are equally useful embodiments of the present disclosure.

In an embodiment of an elastomeric composition suitable for use with the present invention, the glycerol is present in the silicone pre-elastomer at a ratio of glycerol to silicone elastomer of from 0.1 to 1.5 by weight (corresponding to from 10 to 150 phr).

In an embodiment of an elastomeric composition suitable for use with the present invention, the glycerol is present at a ratio of glycerol to silicone pre-elastomer of from 0.2 to 1.4 by weight (corresponding to from 20 to 140 phr), such as a ratio of from 0.3 to 1.2 by weight (corresponding to from to 120 phr), such as from 0.4 to 1.0 by weight (corresponding to from 40 to 100 phr), such as from 0.5 to 0.8 by weight (corresponding to from 50 to 80 phr).

As was established in the prior art, glycerol may be incorporated in a silicone elastomer at high loadings while maintaining glycerol as discrete droplets in the silicone elastomer. Thereby is provided an elastomeric composition in the form of a freestanding thin film without compromising the mechanical properties of the resulting elastomeric composition. As documented in the prior art, discrete droplets of glycerol may be present in the silicone matrix as well as a bicontinuous matrix of glycerol and silicone.

In an embodiment of an elastomeric composition suitable for use with the present invention, the silicone pre-elastomer is selected from the group comprising pre-elastomers of methylsilicone elastomers, phenylsilicone elastomers, chloroalkylsilicone elastomers and fluorosilicone elastomers or combinations thereof.

In an embodiment of an elastomeric composition suitable for use with the present invention, the silicone pre-elastomer is selected from the group comprising pre-elastomers of polyalkylsiloxanes, preferably polydimethylsiloxane (PDMS) and derivatives thereof. Exemplary PDMS pre-elastomers include vinyl-functional PDMS pre-elastomer crosslinkable with hydride-functional crosslinking agents, or hydroxyl-functional PDMS pre-elastomer crosslinkable in the presence of Sn or Pt. Non-limiting examples of commercially available PDMS pre-elastomers include Sylgard® 184 from Dow Corning and Elastosil® RT625 from Wacker Chemie, Germany.

In an embodiment of an elastomeric composition suitable for use with the present invention, the silicone pre-elastomer is a chlorosilicone pre-elastomer. Non-limiting examples of suitable chlorosilicone pre-elastomers are chloroalkyl-based chlorosilicone pre-elastomers, compositions from chloromethyl-terminated polydimethylsiloxanes (e.g. DMS-L21 from Gelest) or chlorosilicone elastomers as disclosed in WO 2015/043792.

In an embodiment of an elastomeric composition suitable for use with the present invention, the silicone pre-elastomer is a fluorosilicone pre-elastomer. Non-limiting examples of commercially available fluorosilicone pre-elastomers are of the Silastic® F-LSR range of elastomers from Dow Corning, the FE/FEA series from ShinEtsu silicones, Krytox from DuPont, or the Elastosil® FLR series from Wacker Chemie.

In an embodiment of an elastomeric composition suitable for use with the present invention, the elastomeric composition further comprises one or more excipients selected from the group consisting of active substances, in particular active substances for human or animal use, in particular drugs, and/or from catalysts, inhibitors, flow agents, silicone oils, solvents, fillers, blowing agents, reinforcing substances, and plasticizers.

In a particularly preferred embodiment of an elastomeric composition suitable for use with the present invention, one or more excipients can be selected from the group consisting of an active substance and/or a drug for human or animal use, the active substance and/or drug is selected from erythrosine B and/or hydroquinone.

In an embodiment of an elastomeric composition suitable for use with the present invention, one or more excipients can be selected from the group consisting of catalysts, such as Pt complexes (addition curing), Sn (condensation curing), peroxide (peroxide curing) and inhibitors, such as divinyltetramethyldisiloxane and 1,3,5,7-tetravinyl-1,3,5,7-tetramethylcyclotetrasiloxane. Examples of commercially available inhibitors are SID4613.0 (1,3-divinyltetramethyldisiloxane) and SIT7900.0 (1,3,5,7-tetravinyl-1,3,5,7-tetramethylcyclotetrasiloxane) from Gelest Inc.

In an embodiment of an elastomeric composition suitable for use with the present invention, the elastomeric composition may further comprise one or more excipients selected from the group consisting of fillers, reinforcing substances, and plasticizers, such as e.g. plasticizer oils for reducing the melt viscosity of the elastomer during its processing, for example, mineral oils comprising known quantities of paraffinic, naphthenic and aromatic molecules, active fillers (e.g. zinc oxide and stearic acid), inactive fillers (such as carbon black, titanium dioxide, silica, carbonates, kaolin, clay and talc), or resins such as Vinyl Q resins from Gelest Inc. Such excipients may be present in a commercially available silicone elastomer or may be added to the silicone elastomer separately.

The amount of excipient necessary can be varied independently depending on the elastomeric composition in question, but usually is in the range from 0 to 40% by weight, such as from 5 to 30% by weight, such as from 10 to 25% by weight of the elastomeric composition.

In an embodiment of an elastomeric composition suitable for use with the present invention, the elastomeric composition may further comprise an excipient selected from the group consisting of flow agents, silicone oils and solvents. Commercially available examples thereof include silicone oil WACKER® AK SILICONE FLUID or a solvent such as OS-20 from Dow Corning®.

In an embodiment of an elastomeric composition suitable for use with the present invention, the elastomeric composition comprises as excipient at least one blowing agent.

In an embodiment of an elastomeric composition suitable for use with the present invention, the at least one blowing agent is present in an amount in the range from 0.1 to 10 phr, such as from 0.2 to 8 phr, such as from 0.3 to 6 phr, such as from 0.4 to 5 phr, such as from 0.5 to 4 phr, such as from 0.6 to 3 phr, such as from 0.7 to 2 phr, such as from 0.8 to 1.5 phr, or such as from 0.9 to 1 phr. Preferably, the at least one blowing agent in present in an amount less than from 1 phr, such as less than from 0.9 phr, such as less than from 0.8 phr.

In an embodiment of an elastomeric composition suitable for use with the present invention, the blowing agent is a base. Non-limiting examples thereof include inorganic bases such as NaOH, KOH, and LiOH; amine based compounds, such as triethanolamine, ethanolamine, triethylamine, ethylamine, methylamine, polyetheramines (such as JeffAmines® commercially available from Huntsman); and phosphazene bases such as BEMP (2-tert-Butylimino-2-diethylamino-1,3-dimethylperhydro-1,3,2-diazaphosphorine), and P1-t-Bu (N,N,N',N',N",N"-hexamethyl-N'''-(2-methyl-2-propanyl) phosphorimidic triamide).

In a particular embodiment of an elastomeric composition suitable for use with the present invention, the blowing agent is NaOH. It was shown in the prior art that surprisingly the addition of NaOH in small amounts as indicated above provides rapid foaming and a foam having small uniform air voids. The present inventors have found that also the multiphase glycerol silicone elastomers of the present invention can foam in a like manner. This is advantageous, since with multiple glycerol phases in the silicone elastomers, one glycerol phase can comprise an excipient, which is labile to bases, while another glycerol phase can comprise the foaming agent, e.g. NaOH, and a foam can then be prepared substantially without loss of activity of the excipient.

In an embodiment of an elastomeric composition suitable for use with the present invention, the elastomeric composition further comprises one or more additives. Depending on the additive in question and its hydrophilic/hydrophobic properties, the additive will be present either in solution or in dispersion in the glycerol droplets or in the silicone elastomer or in both.

In an embodiment of an elastomeric composition suitable for use with the present invention, the one or more additives are selected from the group consisting of coloring substances, pharmaceutical substances, magnetic substances such as e.g. iron, ferrite and magnetite, tracer substances such as fluorescent particles and molecules, labelled molecules (e.g. deuterated) etc. One or more additives may be added in order to impart particular properties to the elastomeric composition, such as coloring, in order to provide e.g. therapeutic properties, or in order to allow controlled release of a pharmaceutical substance.

In an embodiment of an elastomeric composition suitable for use with the present invention, the elastomeric composition possesses a dielectric permittivity at 1 Hz of at least 3.5, preferably at least 5, such as at least 7.5. Thereby electrically enhanced active substance delivery, particularly enhanced drug delivery, can be achieved.

In an embodiment of an elastomeric composition suitable for use with the present invention, the method for preparing an elastomeric composition comprises a step of mixing the silicone pre-elastomer, the at least one crosslinking agent, the glycerol and optionally one or more excipients and optionally one or more additives.

In an embodiment of an elastomeric composition suitable for use with the present invention, the method for preparing an elastomeric composition comprises preparing a silicone premix comprising the silicone pre-elastomer and the at least one crosslinking agent; preparing a glycerol premix optionally comprising one or more excipients and optionally one or more additives; and mixing the silicone premix and the glycerol premix through the application of shear at a level of from about 1000 rpm to about 5000 rpm.

In an embodiment of an elastomeric composition suitable for use with the present invention, the method for preparing an elastomeric composition comprises a step of preparing a silicone premix comprising the silicone pre-elastomer and the at least one crosslinking agent; preparing a glycerol premix comprising glycerol and at least one excipient in the form of a blowing agent; and mixing the silicone premix and the glycerol premix.

In an embodiment of an elastomeric composition suitable for use with the present invention, the blowing agent is a base. In some embodiments the blowing agent is a strong base such as NaOH, preferably, however, a weak base should be used as a blowing agent to minimize or even prevent base-catalyzed degradation of the formed and cured silicone matrices.

In an embodiment of an elastomeric composition suitable for use with the present invention, the silicone elastomer foam is an expanded elastomeric composition having a specific gravity in the range of 0.05 to 0.5 g/cm3, such as 0.1 to 0.4 g/cm3, such as 0.1 to 0.3 g/cm3, or such as 0.1 to 0.25 g/cm3.

In an embodiment of an elastomeric composition suitable for use with the present invention, the method comprises mixing in step v) performed at a shear level of from about 1500 rpm to about 4000 rpm, such as from about 2000 rpm to about 3500 rpm.

Figure 14:
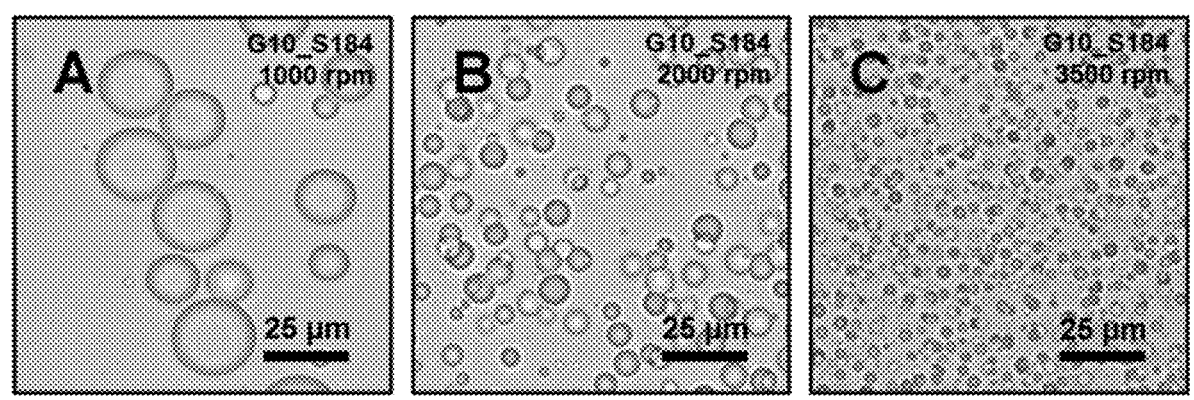
FIG. 14: Optical microscopy images of 10 phr glycerol in S184 emulsions obtained after 5 minutes of speed-mixing at 1000 (A), 2000 (B) and 3500 (C) rpm. Scale bars correspond to 25 μm.

FIG. 14 discloses the influence of shear rate on the size distribution of the glycerol globules in the elastomeric composition, showing how the glycerol globule diameter varies between globule diameters ranging up to about 25 µm (1000 rpm, A), up to about 7.5 µm (2000 rpm, B) and up to about 4 µm (3500 rpm, C).

Curing of the silicone pre-elastomer may take place as known in the art.

In an embodiment of an elastomeric composition suitable for use with the present invention, the method comprising curing takes place in the form of addition-based curing, such as by the use of Pt as a catalyst, wherein Si—H groups of the crosslinking agent react with vinyl groups of the silicone prepolymer.

In another embodiment an elastomeric composition suitable for use with the present invention, the method comprising curing takes place in a condensation-based system, such as through the use of a Sn-based curing system and a room-temperature vulcanizing silicone pre-elastomer, wherein an alkoxy crosslinker experiences a hydrolysis step and is left with a hydroxyl group participating in a condensation reaction with another hydroxyl group attached to the polymer in question.

In another embodiment of an elastomeric composition suitable for use with the present invention, the method comprising curing takes place in a peroxide-based system, wherein an organic peroxide compound decomposes at elevated temperatures to form reactive radicals that chemically crosslink the polymer chains. A commercially available crosslinking agent is ELASTOSIL® AUX curing agent C1 from Wacker AG.

In an embodiment of an elastomeric composition suitable for use with the present invention, the method comprising curing takes place through the application of energy, preferably wherein the energy is heat or radiation. Whereas application of energy may not be necessary, in particular not for room temperature vulcanizing silicone elastomers, heating may accelerate the curing process.

In an embodiment of the invention, curing is by heating. When heating is applied, curing is at a temperature of curing between from 50° C. to 250° C., between from 60° C. to 200° C., between from 70° C. to 175° C., between from 80° C. to 150° C., between from 90° C. to 125° C. or between from 100° C. to 110° C. Particularly preferred are temperatures of curing between from 50° C. to 100° C. as losses of silicone and glycerol to evaporation are negligible in this temperature range. Particularly 80° C. has been found to provide a suitable compromise between reasonable curing rate and negligible loss of silicone and glycerol to evaporation.

The mixture may be cured over a broad range of temperatures and may subsequently be stored over a long time without evaporation of liquid phase.

The present inventors have surprisingly discovered that the delivery rate of an active substance comprised in the glycerol phase in the cured elastomeric silicone composition can be influenced and controlled by controlling the glycerol silicone composition morphology and that thereby reversibly compositions can be provided varying between zero-order to first-order release kinetics. In particular, it has been surprisingly discovered that the compositions showing at least near-zero-order active substance release kinetics do not exhibit an initial active substance release burst.

In the present disclosure, a release kinetic for an active substance comprised in a glycerol phase is described as near-zero-order, if the release rate of the active substance from the cured glycerol-silicone elastomer is substantially constant until at least 60% of the active substance comprised in the system has been released from the cured glycerol-silicone elastomer, preferably is substantially constant until at least 70%, at least 75%, at least 80%, at least 85%, or at least 90% of the active substance comprised in the system has been released from the cured glycerol-silicone elastomer.

In the present disclosure, a release kinetic for an active substance comprised in a glycerol phase is described as zero-order, if the release rate of the active substance from the cured glycerol-silicone elastomer is substantially constant until at least 91% of the active substance comprised in the system has been released from the cured glycerol-silicone elastomer, preferably is substantially constant up till at least 93%, at least 95%, at least 96%, at least 97%, or at least 98% of the active substance comprised in the system has been released from the cured glycerol-silicone elastomer.

In particular there is disclosed according to the invention an active substance-release silicone elastomer composition having at least near-zero-order active substance release kinetics and comprising at least one distinct glycerol phase enclosed in a continuous silicone elastomer matrix, wherein an active substance to be released is comprised in the at least one distinct glycerol phase, and the at least one distinct glycerol phase is present to at least 60 phr in the silicone elastomer matrix.

Also according to the invention there is disclosed, an active substance-release silicone elastomer composition having at least near-zero-order active substance release kinetics according to the embodiments disclosed herein, the wherein the at least one distinct glycerol phase is present to between from 60 phr to 150 phr, to between from 70 phr to 140 phr, to between from 80 phr to 130 phr, to between from 90 phr to 120 phr, or to between from 100 phr to 110 phr in the silicone elastomer matrix.

Also according to the invention there is disclosed, an active substance-release silicone elastomer composition having at least near-zero-order active substance release kinetics according to the embodiments disclosed herein, wherein when the at least one distinct glycerol phase is present in a concentration of from 100 phr to 150 phr, preferably of from 110 phr to 130 phr, and most preferably to a concentration of 120 phr in the silicone elastomer matrix, active substance release observing zero-order active substance release kinetics is obtained.

Also according to the invention there is disclosed, an active substance-release silicone elastomer composition having at least near-zero-order active substance release kinetics according to the embodiments disclosed herein, wherein at least two distinct glycerol phases, each distinct glycerol phase comprising a respective active substance to be released, are enclosed in the continuous silicone elastomer matrix, with the proviso that the total concentration of glycerol in the silicone elastomer composition is present to between from 60 phr to 150 phr, to between from 70 phr to 140 phr, to between from 80 phr to 130 phr, to between from 90 phr to 120 phr, to between from 100 phr to 110 phr in the silicone elastomer matrix, preferably is present to between from 80 phr to 130 phr.

Also according to the invention there is disclosed, an active substance-release silicone elastomer composition having at least near-zero-order active substance release kinetics according to the embodiments disclosed herein, wherein the silicone elastomer composition is a cured elastomeric silicone composition according to any of the embodiments disclosed herein.

Also according to the invention there is disclosed, an active substance-release silicone elastomer composition having at least near-zero-order active substance release kinetics according to the embodiments disclosed herein, wherein a dimension of the active substance-release silicone elastomer composition is between from 0.1 mm to 5 mm. Thereby patches for transdermal active substance delivery can be provided, when the active substance to be released is an active substance that can be transdermally delivered, in particular wherein the active substance is a drug.

According to the invention there is further disclosed a method of changing an active substance release kinetics reversibly between zero-order active substance release kinetics and first-order active substance release kinetics for an active substance-release silicone elastomer composition comprising at least one distinct glycerol phase enclosed in a continuous silicone elastomer matrix, wherein an active substance to be released is comprised in the at least one distinct glycerol phase, the method comprising adjusting the concentration of glycerol in an elastomeric silicone composition of a distinct glycerol phase comprising at least one active substance to be released from the glycerol phase above or below a first glycerol concentration threshold; speed-mixing the elastomeric silicone composition and distinct glycerol phase at between from 1000 rpm to 5000 rpm; and subsequently curing the resulting mixture.

Also according to the invention there is disclosed, a method of changing an active substance release kinetics reversibly between zero-order active substance release kinetics and first-order active substance release kinetics for an active substance-release silicone elastomer composition according to the embodiments disclosed herein, wherein the first glycerol concentration threshold is 60 phr glycerol total concentration of glycerol in the silicone elastomer composition.

Also according to the invention there is disclosed, a method of changing an active substance release kinetics reversibly between zero-order active substance release kinetics and first-order active substance release kinetics for an active substance-release silicone elastomer composition according to the embodiments disclosed herein, wherein the elastomeric silicone composition is an active substance-release silicone elastomer composition according to the embodiments disclosed herein.

Also according to the invention there is disclosed, a method of changing an active substance release kinetics reversibly between zero-order active substance release kinetics and first-order active substance release kinetics for an active substance-release silicone elastomer composition according to the embodiments disclosed herein, wherein an active substance release rate of an active substance comprised in a distinct glycerol phase comprised in the elastomeric silicone composition is adjusted by adjusting a cross-linking density during curing of the elastomeric silicone composition and/or is adjusted by changing a morphology of the resulting mixture of glycerol and elastomeric silicone composition.

EXAMPLES

All silicone compositions comprising a glycerol phase were prepared as according to steps i. to v. of WO 2016/189117 as reproduced in the present disclosure.

Materials

Two-component Sylgard 184 silicone kit (S184), i.e. divinyl-terminated polydimethylsiloxane comprising a crosslinker as well as a Pt catalyst with silica as reinforcing agent, was purchased from Dow Corning. Glycerol (food grade) being a byproduct from biodiesel production was provided by Emmelev A/S and was used as received avoiding excessively long contact with air.

Equipment

A dual asymmetric centrifuge SpeedMixer DAC 150 FVZ-K was used for mixing of all compounds. A Leica DM LB optical microscope was applied for investigation of glycerol in silicone emulsion morphology.

Methods

A Sylgard 184 silicone kit (S184) was mixed in ratio 10:1 by weight as recommended by the manufacturer. Subsequently the desired amount of glycerol was added to PDMS and stirred with the help of the speed-mixer for 5 minutes at 3500 rpm unless mentioned otherwise. In some instances, after the mixing step, compositions were cast onto a metal mold with a 1 mm spacer and cured at 80° C. for 1 hour. Obtained films were then left at room temperature for at least two days for eventual post-curing to take place.

Example 1: Preparation of Multi-Compartment Glycerol-Silicone Elastomers

Experimental

A colorant was added to glycerol, and the resulting glycerol composition mixed with a Sylgard silicone composition by speed-mixing at 3500 rpm for 5 min until a homogeneous solution was obtained. Thereby a silicone composition comprising a single glycerol phase was prepared. The composition was in the form of an emulsion.

Two or three different emulsions, each having a distinct colorant (red/blue/green) dissolved in their respective glycerol phases were gently transferred to a larger container and mixed at a comparatively low mixing speed of 500 rpm for 1 minute. Faster mixing, above 1000 rpm, resulted in merging of the glycerol droplets. The presence of thinners (e.g. solvents) and/or surfactants in the glycerol phase lowers the mixing speed at which merging of the droplets occurs.

The mixed emulsions were then crosslinked for 10 minutes at 100° C. followed by 2 minutes at 200° C. to form a cured elastomeric silicone composition.

Results

FIG. 1 details dual compartment silicone elastomer emulsions as thin films under an optical microscope, prior to curing. The films comprise two distinct glycerol phases characterized therein, that each glycerol phase is distinct by the presence of different excipients, the excipients being either a blue colorant (FIG. 1A) or a red colorant (FIG. 1B). FIG. 1C shows the elastomeric composition after mixing, wherein it can be observed that the colorants remain separated in the glycerol globules and that hence the elastomer comprises two distinct glycerol phases.

FIG. 2 details the cured silicone elastomer (1 mm thickness) showing a blue band (left) a purple band (center) and a red band (right) proving homogenous mixing of the two colored phases prior to curing without merging of droplets of different phases and the maintenance of homogeneity after curing.

FIG. 3 details a triple compartment silicone elastomer emulsion as a thin film under an optical microscope, prior to curing and comprising three distinct glycerol phases characterized therein that each glycerol phase is distinct by the presence of different excipients, the excipients being either a blue colorant, a red colorant, or a green colorant. The yellow color present is an artefact from out-of-focus plane green light. Hence, yellow droplets are in fact green.

As observed, different types of glycerol droplets do not interact with each other as they are separated by the silicone.

Advantageously thereby, by testing with dual or multiple compartment glycerol phases, each phase comprising a distinct colorant, followed by speed mixing and visual inspection as detailed in the present example, there is provided a simple test for mixing shear upper and lower limits. If the differently colored glycerol phases coalesce, this is directly discernable in a microscope as color changes, which again is directly indicative of the shear having been excessive for the mixing purpose. Thereby, upper shear limits can be established. Likewise, failure to mix, as observed by visual inspection is directly indicative of the mixing shear force having been too low.

Advantageously, this observation can further be exploited in the present invention. E.g. where excipients and active substances are intended to be used, e.g. for drug delivery, but wherein the excipients or the active substances are not in their own right colorants, or wherein a particular active substance e.g. is very costly (e.g. a medical drug), a test system with colorants can be prepared initially and optimized mixing shear rates established following the above method, simply by visual inspection.

In the above example, visual inspection was performed with visible light; however, UV- or IR-excitation of colorants, followed by false-color imaging in the visual spectrum is equally suitable.

Example 2: Release of Active Substances From a Single Compartment Glycerol-Silicone Elastomer Comprising Hydroquinone Sample Preparation The example provided leads to a 1.42 g batch of material that may readily be scaled up or down. Using the described method batches from between 1 g and 80 g were prepared. Hydroquinone (HQ, 0.02 g, 5 wt. %) was dissolved in glycerol (0.4 g) at 50° C. using magnetic stirring until a clear solution was obtained (typically around 1-2 hours). Desired amounts of S184 (formed by combining the base 0.909 g and curing agent 0.091 g in a 10:1 mix following the manufacturer's guidelines, or 0.952 g of the base and 0.048 g of the curing agent in a 20:1 mix to give less crosslinked products) and glycerol/hydroquinone (the ratios of the glycerol/silicone products were the same irrespective of the presence of hydroquinone) were mixed at 3500 revolutions per minute (rpm) for 5 min using a dual asymmetric centrifuge Speed-Mixer DAC 150 FVZ-K. The obtained glycerol-in-silicone emulsions were cast onto a metal mold with 1 mm thick spacer or coated with various commercial knives in order to obtain films with thicknesses of around 0.1, 0.2, 0.3, 0.4 or 0.5 mm, respectively. The samples were subsequently cured at 80° C. for 1 h. Circular disc samples were cut using a custom-made die (25 mm in diameter and 1 mm thick). Thinner samples were cut out by hand into 4.5×4.5 cm rectangles using a laboratory knife. Sample nomenclature uses the pattern GX HQY S184 Z, where G and X correspond to glycerol and concentration of glycerol in phr (weight parts per hundred weight parts of silicone elastomer), HQ and Y correspond to hydroquinone and concentration of hydroquinone dissolved in glycerol (expressed as weight percentage of HQ in glycerol) and S184 corresponds to applied silicone composition, respectively. Z accounts for varying material parameters that are discussed below. A full description of all investigated samples with corresponding sample names can be found in Table 1. Compositions based on glycerol, silicone (Sylgard 184 in a 10:1 mix ratio) speed-mixed at 3500 rpm are considered as basic samples. Extensions of the basic compositions are marked bold in the table.

Methods

Film thicknesses were measured using an optical microscope Leica DM LB. A FEI Quanta 200 ESEM FEG scanning electron microscope (SEM) was used to investigate the morphologies of composites. Prior to testing, the cross-sections were coated under vacuum conditions and a current of 20 mA for 5 s for depositing a 2 nm-thick gold layer using a high resolution sputter coater Cressington 208HR.

Figure 4:
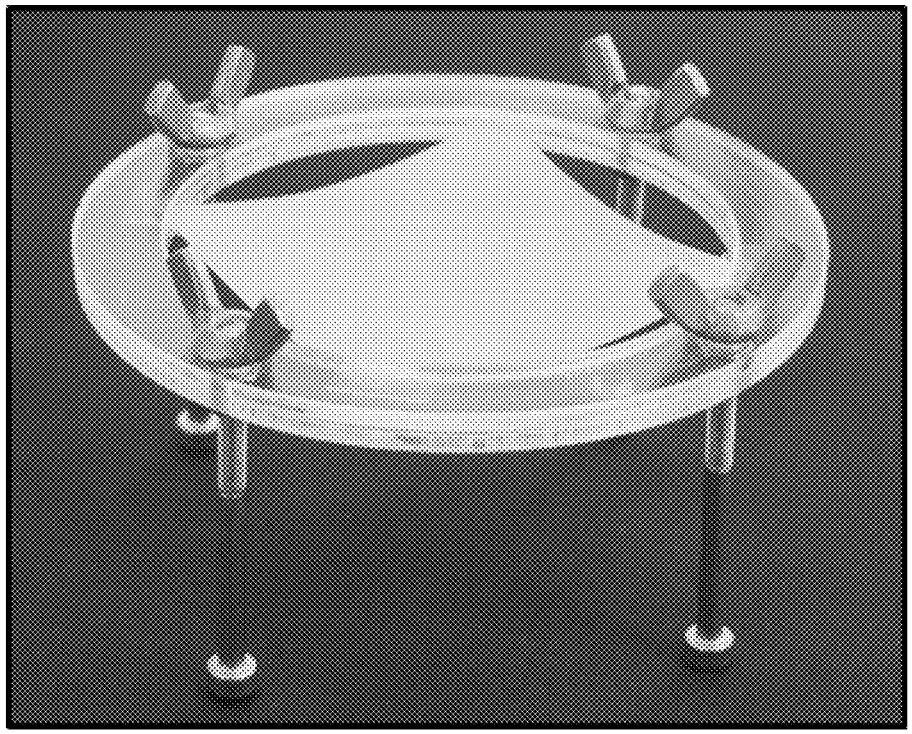
FIG. 4: Test stage for release profile study.

Release profiles of HQ from the glycerol-silicone elastomers were determined by immersing composites containing various amounts of glycerol with 5 wt % of HQ in deionized water. The progress of hydroquinone release was monitored by measuring changes in concentration of hydroquinone in the aqueous environment. A UV-vis spectrophotometer POLARstar Omega microplate reader by BMG LabTech was used for the tests, and outcomes were compared against a calibration curve for hydroquinone/water solutions. Each release profile curve represents an average of three separate experiments. The 1 mm thick disc samples were tested in tightly sealed conical flasks (placed on a rotary shaker) in order to avoid water evaporation in cases where the measurements lasted for a substantial amount of time. The thinner films (0.1-0.5 mm) tend to self-adhere when exposed to water therefore they were mounted onto custom-made frames (FIG. 4) to maintain a constant exposed surface area and placed in beakers equipped with magnetic stirring. The water evaporation rate proved to be negligible (<1.5% per 8 h), therefore, no corrections to the calculations on HQ concentrations were necessary.

Active Substance Release

Hydroquinone was used in this study as a model compound—an easily "traceable" active substance—to investigate release profiles from the glycerol-silicone elastomers. The experiments were conducted until no further increase in hydroquinone concentration in the external water phase was observed. The values obtained from plateau regions of the release profiles were considered to correspond to the full release of hydroquinone from the glycerol-silicone composites. Maximum releases of, on average, 93% (±4%) of the theoretical value based on mass of incorporated hydroquinone, glycerol loading and measured film thickness were achieved.

The water absorption study indicates indirectly that there are several factors influencing release rates of substances from the composites. The results of the experiments presented in this section are meant to provide an overview of different parameters that influence the release rather than to suggest optimization of ultimate matrix properties, as it is believed that the technology allows for the preparation of numerous products with various properties that can be adapted for different applications.

Influence of Glycerol Loading on Release Profiles

Figure 5:
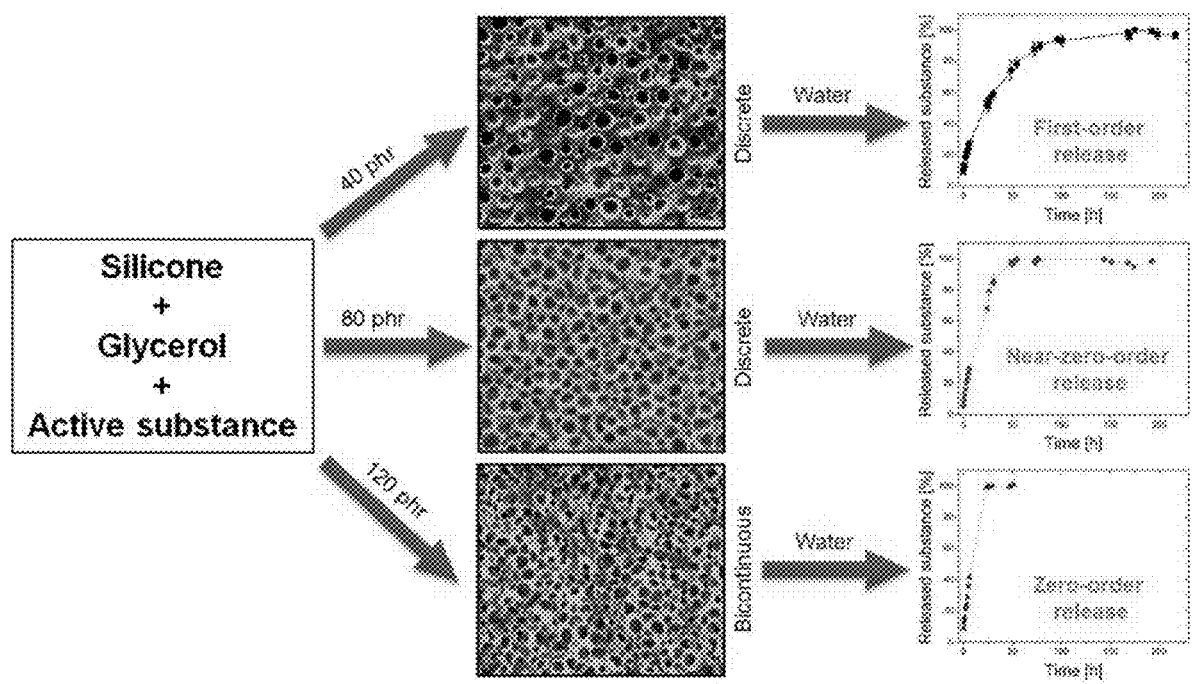
FIG. 5: Relation between morphology and release profile.

In FIG. 5 there is disclosed data on the influence of glycerol loading on the morphology and release kinetics of the glycerol-silicone elastomers. The release profiles of hydroquinone from various 1 mm thick glycerol-silicone elastomers are presented. By increasing the glycerol content, a transition from a discrete droplet morphology to a bicontinuous structure can be observed. The transition from discrete droplets to bicontinuous is, while gradual, observed experimentally to be complete at about 120 phr glycerol in the matrix.

Upon contact with aqueous media, it was found that the composites release active substances, in the present experiment hydroquinone, with different modes varying between first-order release and zero-order release.

Results presented in FIG. 5 indicate that substances are released faster from composites with higher glycerol loadings, which is in good agreement with findings from water absorption experiments by the present inventors, published previously.[18] The samples comprised 40 phr glycerol (G40_HQ5_S184_1mm), 80 phr glycerol (G80_HQ5_S184_1mm) and 120 phr glycerol (G120_HQ5_S184_1mm), 5 wt % hydroquinone in glycerol, and each had a thickness of 1 mm in the direction of diffusion. The samples released 100% of incorporated hydroquinone after around 1, 2 and 7 days, respectively, with the elastomer having the highest loading of glycerol releasing its hydroquinone the fastest (i.e. 1 day). Interestingly, the same sample comprising 120 phr glycerol (G120_HQ5_S184_1mm) released hydroquinone at a constant rate, exhibiting a zero-order release profile.

It is believed that this behavior is facilitated by the existence of interconnected glycerol channels. Active materials with zero-order or near zero-order release profiles are of great interest, as they allow the delivery of active substances without the common 'burst effect' in which a significant amount of an active substance is released in the initial stage of the process.[3,4,22] This is a significant advantage over conventional first- and second-order active substance delivery systems as zero (and near-zero) order drug delivery systems allow for a full control over the release process.[23,24]

Influence of Glycerol Globule Sizes on Release Profiles

Figure 6:
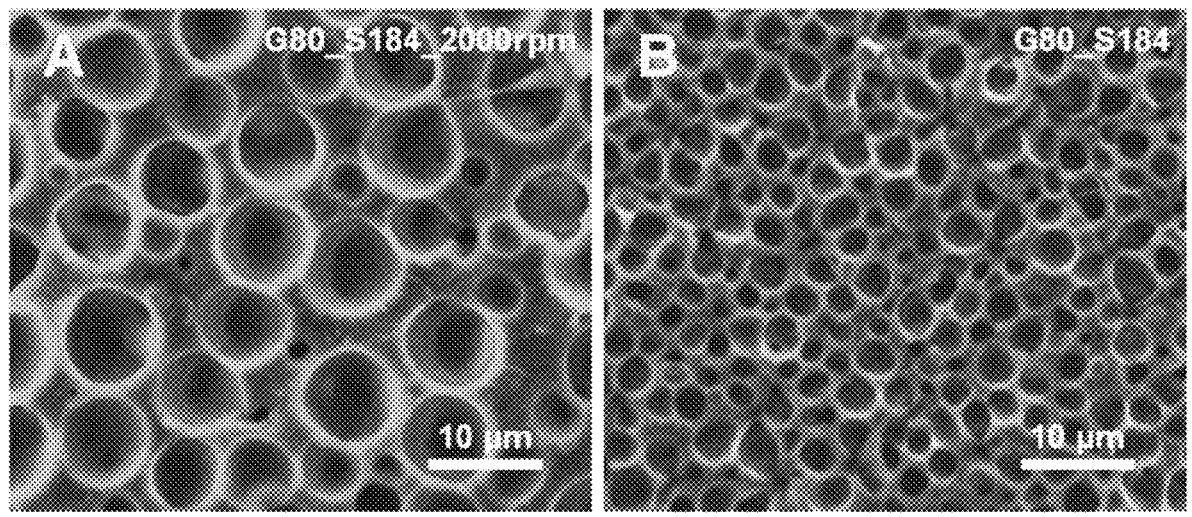
FIG. 6: SEM images of cured elastomers based on G80_S184 formulation mixed at 2000 rpm (A) and 3500 rpm (B) before curing.

As discussed in prior work by the inventors,[18] the glycerol globule size can be tuned via controlling the applied shear rate when preparing glycerol-in-silicone emulsions by preparing the compositions at different mixing speeds (c.f. e.g. FIGS. 6 and 14).

FIG. 6 discloses a composition with 80 phr of glycerol exposed to mixing at 2000 rpm or 3500 rpm for two minutes resulting in formation of composites with average glycerol droplet diameters of 5.9 μm and 2.5 μm, respectively. SEM images of the composites are presented in FIG. 6. FIG. 14 discloses optical microscopy images of 10 phr glycerol in S184 emulsions obtained after 5 minutes of speed-mixing at 1000 (A), 2000 (B) and 3500 (C) rpm. Scale bars for all images correspond to 25 μm. As observed, also glycerol concentration at a given shear rate influences the globule diameter.

Figure 7:
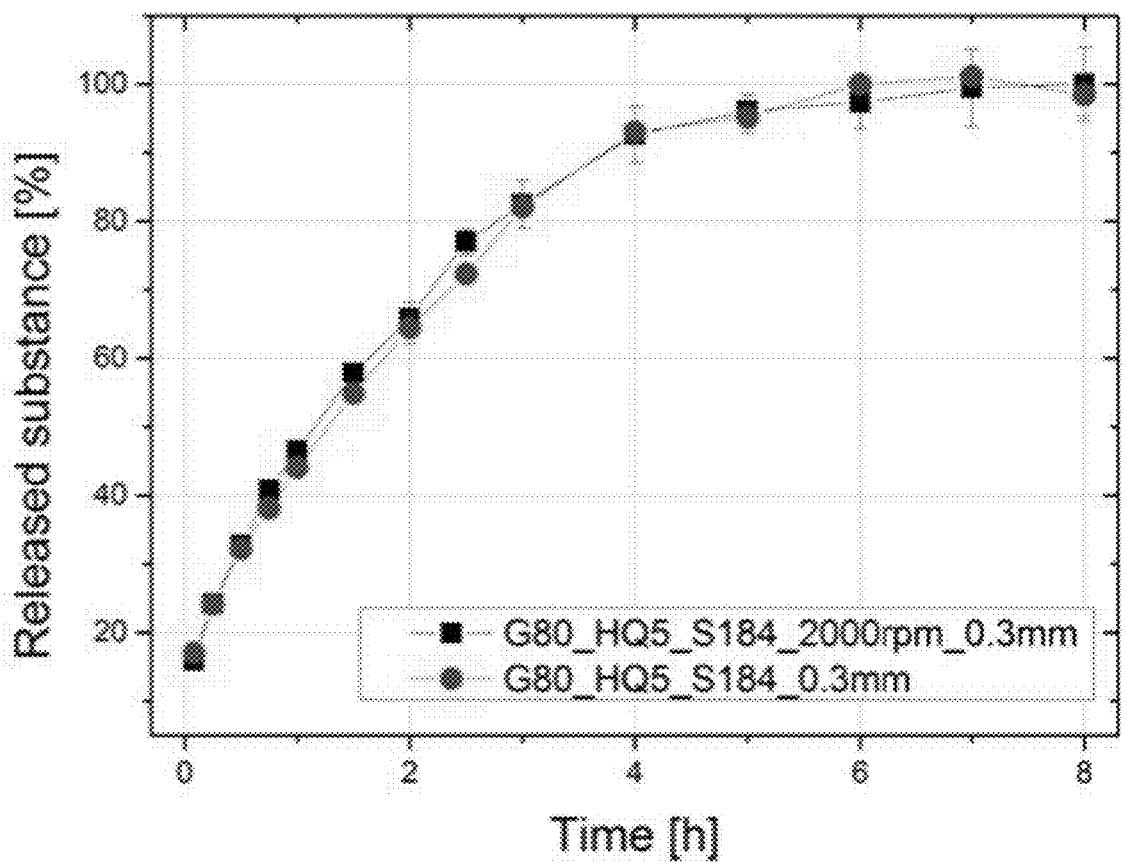
FIG. 7: Release profiles of samples based on the formulation G80_HQ5_S184 prepared using different mixing speeds.

While it was speculated that the droplet size might influence the release of hydroquinone the release profiles of the investigated samples were almost identical despite the difference in overall glycerol-silicone interface area in the samples, c.f. FIG. 7.

Without being bound by this theory, the inventors speculate that osmotic potential is the main factor that influences release and release rate in the systems of the invention. A positive use of this fact is that lower shear forces can be applied in order to produce emulsions that become a basis for creating elastomer matrices exhibiting desired release behavior as demonstrated herein above and below for the multi-compartment elastomers of the invention.

Influence of Cured Elastomer Thickness on Release Profiles

Figure 8:
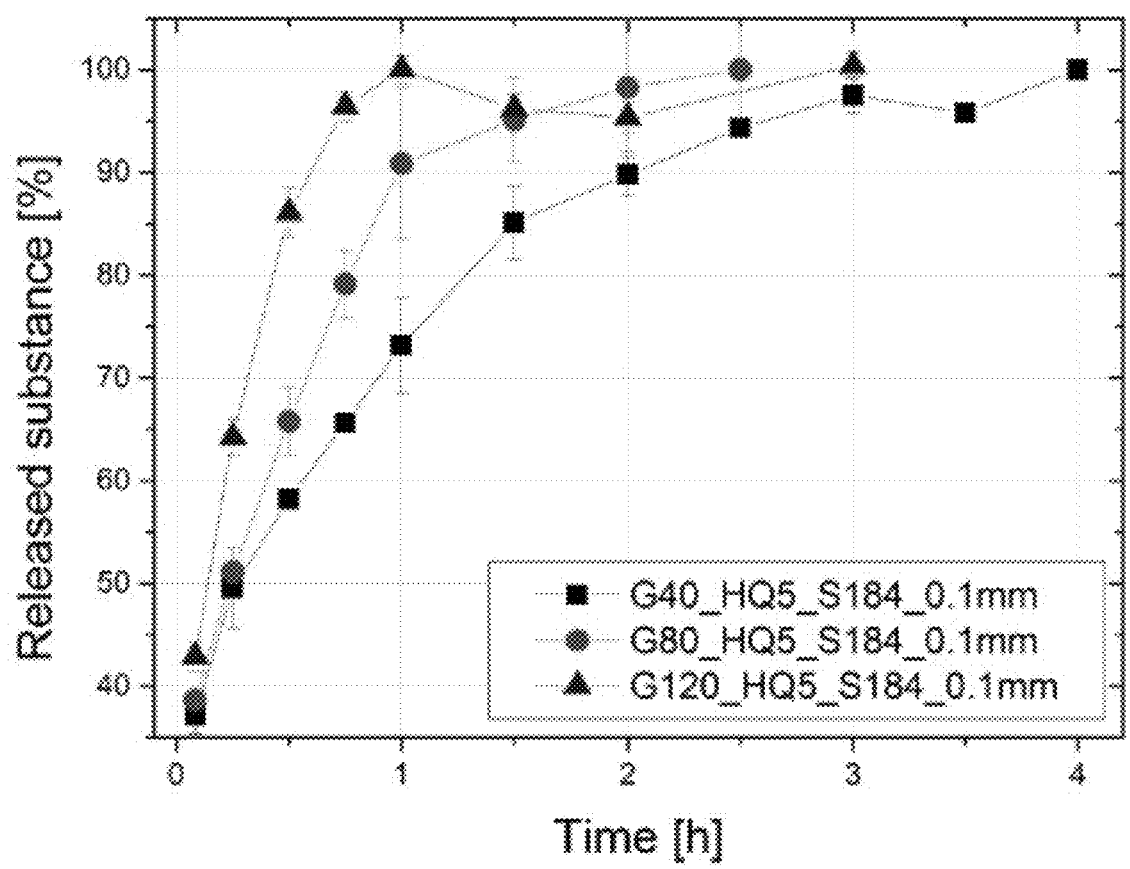
FIG. 8: Hydroquinone release profiles from various 0.1 mm thick glycerol-silicone elastomers in dependence of glycerol loading.

The release rates were shown to vary as a function of the surface area/thickness ratio. For example, release profiles analogous to those of the 1 mm thick samples were observed in the case of 0.1 mm composite films (FIG. 8). The complete release of hydroquinone from the sample G80_HQ5_S184_0.1mm was reached after around 2 to 2.5 hours, whereas the 10 times thicker sample needed as much as around 50 hours to release the whole content of hydroquinone. As commented on in relation to FIG. 5, the release kinetics approach zero order as the glycerol loading is increased in response to the change from a discrete globular structure of the glycerol domains to a bicontinuous matrix at 120 phr.

Figure 9:
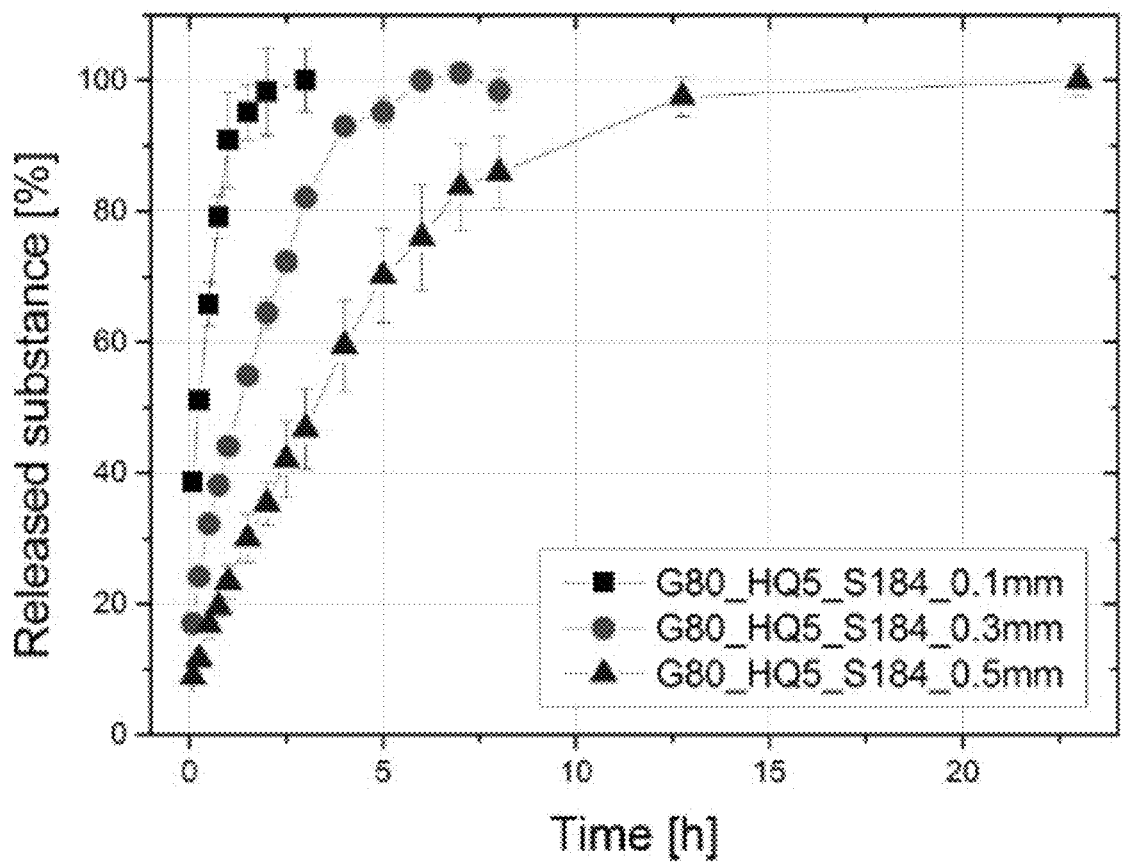
FIG. 9: Hydroquinone release profiles from glycerol-silicone elastomers of various thicknesses and constant glycerol loading.
Figure 10:
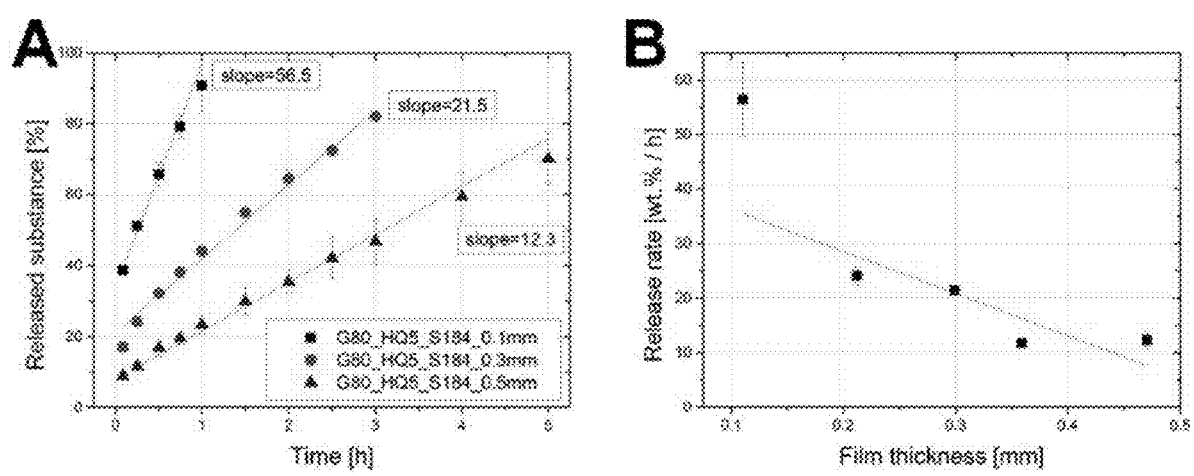
FIG. 10: Comparison of release rates of samples with 80 phr of glycerol and different thicknesses. (A) Slopes of the release profiles of various samples. (B) Dependence of the release rate on the film thickness for compositions G80_HQ5_S184.

In FIG. 9, release data for different composite thicknesses at constant glycerol loading is shown. The data clearly shows that the release profiles of the investigated composites exhibit strong dependence on composite thickness. The entire content of hydroquinone was depleted after around 3, 7 and 23 hours from 0.1, 0.3 and 0.5 mm thick films, respectively, suggesting a non-linear dependence of release time and film thickness, which is typical for non-zero-order release processes. However, it can be realized that the samples released hydroquinone with constant rates in the first stage of the release process (up to 70-90%) indicating existence of near zero-order release kinetics. The release rates were estimated by calculating slopes of the curves as presented in FIG. 10A. The release rates were fitted against thicknesses (see FIG. 10B) presenting almost linear dependence indicating near zero-order release kinetics.

Influence of Mechanical Properties on Release Rate

In the presence of water (by water absorption into glycerol); the silicone phase of the composites with discrete glycerol domain morphology are stretched as the glycerol domains swell. Consequently, it is to be expected that the silicone spacing between adjacent droplets becomes thinner, facilitating faster mass transportation within the material and consequently a faster release of substances from within the material as discussed for the water absorption experiments in previous sections.

To test this hypothesis, the present inventors studied the influence of mechanical restrictions to the elastomer, such as e.g. cross-linking, on release rate. Without being bound by this theory, the present inventors consider, that the substance release rate from low-modulus compositions would be accelerated compared to higher-modulus compositions, because of more facile water absorption.

Herein is reported a study of the hydroquinone release from samples based on S184 mixed in different base:crosslinker ratios (10:1 and 20:1) and containing 80 phr of glycerol.

Figure 11:
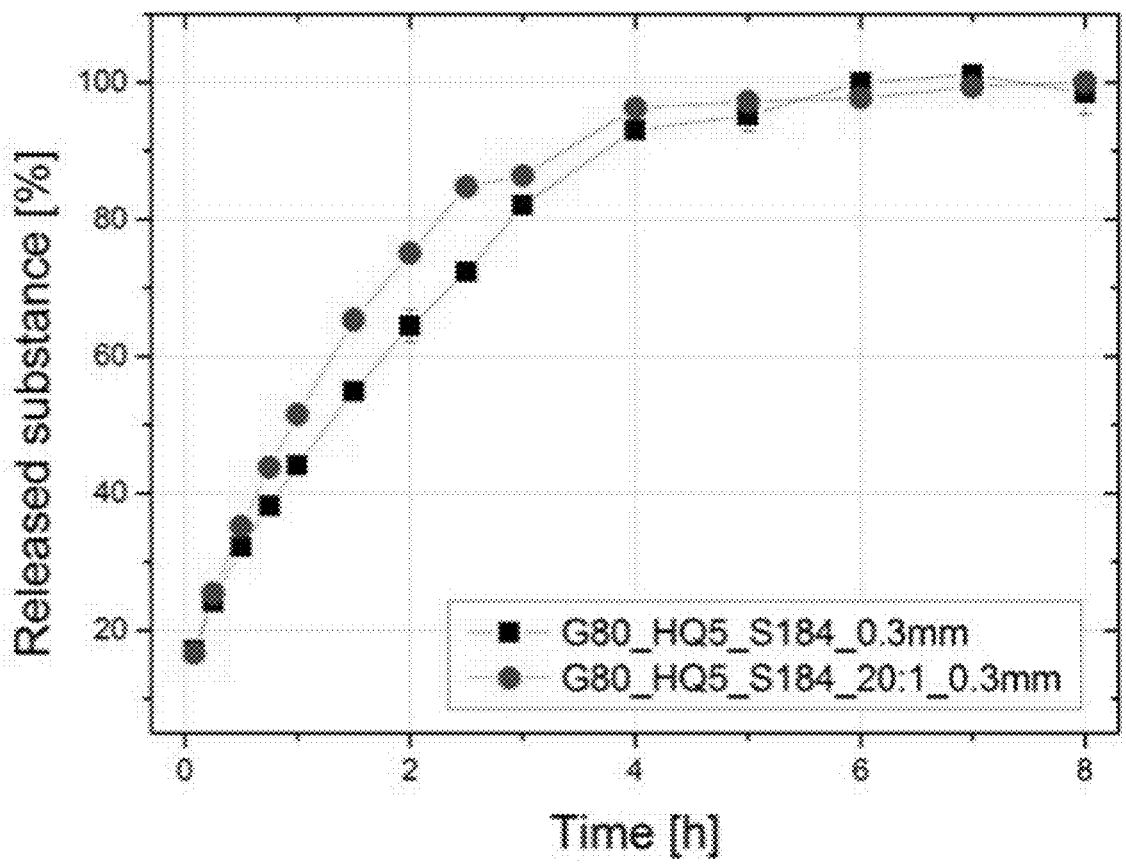
FIG. 11: Release profiles of samples based on the formulation G80_HQ5_S184 using Sylgard 184 mixed in ratios 10:1 and 20:1 (base:crosslinker).

The release curves presented in FIG. 11 clearly indicate that faster release of hydroquinone occurred from the low-modulus composition. After 2.5 hours, the high-modulus sample had released 72% of hydroquinone while the low-modulus sample released 85%. It is expected that it should be possible to tune more narrowly the release rate simply by modifying the structure of the elastomer once a particular structural morphology of the elastomer to glycerol matrix has been decided on.

The active substance release experiments clearly demonstrate that the active substance delivery rate can be tuned simply by altering various formulation parameters during glycerol-silicone composite preparation. Depending on the glycerol loading zero-order, near zero-order and first-order release kinetics can be achieved. Additionally, the active substance release rate can be adjusted by changing film thickness and mechanical properties of the silicone matrix.

The samples with the highest glycerol loadings are especially interesting as they represent a unique example of active substance delivery technology exhibiting zero-order release behavior. Next to the exceptional release function, the technology is biocompatible and can be based on bio-based substrates and, foremost, it is cost-efficient, easy to implement and upscale. The glycerol-silicone elastomer matrices represent a novel family of two-phase elastomers that appears suitable for the wound care industry where smart functionalized materials are required.

Conclusions

Two-phase glycerol-silicone elastomeric composites with surprising functionality were prepared. Simple manipulation of the formulation allows one to control, at will, water absorption and substance release capabilities; the mechanical properties of the silicone elastomer can also be controlled. Most importantly, the matrices offer zero-order, near zero-order and first-order release behavior depending on the glycerol loading within the PDMS elastomer. Additionally, it was proven experimentally, that by modifying various properties (mechanical properties or film thickness), the release rate of the active substances could be precisely controlled.

Example 3: Release of Active Substances From a Dual Compartment Glycerol-Silicone Elastomer Experimental Dual compartment glycerol-silicone elastomers were prepared in four steps. The example presented herein below illustrates preparation of a dual compartment glycerol-silicone elastomer containing erythrosine B and hydroquinone as active substances, each in a respective, distinct glycerol phase. The amounts of all compounds are given by example and can be scaled up or down in accordance with actual need.

At least one glycerol miscible or soluble excipient was added to glycerol in a given concentration and stirred with a mechanical agitator until a uniform and clear solution was obtained. In some cases, stirring at elevated temperatures was required in order to dissolve an active excipient. A solution obtained in this way will form one type of glycerol compartments.

Incorporation of an Active Substance into Glycerol

For the present experiment two solutions were prepared— glycerol-erythrosine B and glycerol-hydroquinone solutions. Glycerol-erythrosine B solution contained 4 g of glycerol and 0.04 g of erythrosine B. Glycerol-hydroquinone solution contained 4 g of glycerol and 0.2 g of hydroquinone. Single emulsions were prepared as detailed above and were subsequently used to prepare two distinct glycerol-in-silicone emulsions. The glycerol-erythrosine B and glycerol-hydroquinone solutions were each added to 5 g of a silicone prepolymer in respective, separate containers. In this case, Sylgard 184 silicone kit from Dow Corning was applied. The respective mixtures were subsequently speed-mixed for 2 to 5 minutes using a dual asymmetric centrifuge DAC SpeedMixer.

Test samples were prepared comprising single compartment silicone elastomers (erythrosine B or hydroquinone) which were cured as below, or mixed, dual compartment silicone elastomers prepared as below.

To prepare the dual compartment silicone elastomers, the two glycerol-in-silicone emulsions were combined. Desired amounts of each of the emulsions were placed into a speed-mixing cup. The composition was subsequently speed-mixed at low mixing rates (typically between from 500 to 1000 rpm) for around 1 minute in order to uniformly distribute both types of droplets within the silicone matrix. Stable emulsions can be mixed with any given speed. It was found to be crucial to maintain low mixing speeds since too high shear forces would usually lead to merging of the two types of glycerol droplets. After combining and mixing both single emulsions a dual compartment emulsion was obtained. The emulsion contained 10 g of silicone, 4.04 g of glycerol droplets containing erythrosine B and 4.2 g of glycerol droplets containing hydroquinone. The total mass of the emulsion was 18.24 g.

In a final step, the elastomer emulsions were cured at 80° C. for 1 hour. Long exposure to high temperatures results in glycerol evaporation therefore prolonged high temperature curing should be avoided. For example, a sample with 80 weight parts of glycerol per 100 parts of silicone cured at 200° C. for 1 hour was observed to lose around 1 wt % of the total mass of the silicone and around 30 wt % of the total mass of glycerol. Mass loses from the same sample cured at 80° C. for 1 h were found to be negligible.

Release Profiles

Release profiles of erythrosine and hydroquinone from the glycerol-silicone elastomers were determined by immersing composites in deionized water. The progress of release of erythrosine B and hydroquinone was monitored by measuring changes in concentration of both compounds in the aqueous environment. A UV-vis spectrophotometer POLARstar Omega microplate reader by BMG LabTech was used for the tests, and outcomes were compared against calibration curves for erythrosine B/water and hydroquinone/water solutions. Each release profile curve represents an average of three separate experiments. Films with thickness of 0.3 mm were investigated. Such thin films tend to self-adhere therefore they were mounted onto custom-made frames (FIG. 4) to maintain a constant exposed surface area and placed in beakers equipped with magnetic stirring.

The silicone elastomer containing 40 phr of glycerol with incorporated erythrosine B and 40 phr of glycerol containing hydroquinone (80 phr of glycerol in total) was tested. Release kinetics comparable to the release from single compartment glycerol-silicone elastomers was expected. Such elastomers exhibit a zero-order release in the first stage of the process, which changes to the first-order release in the second stage. The choice of 80 phr glycerol in total was made to ascertain that the concentration of glycerol in silicone was below the formation threshold for a bicontinuous phase, thereby preventing glycerol globules with hydroquinone or erythrosine B from fusing and thereby influence the observed release behavior.

Nevertheless, it was surprising to observe that the release kinetics did not change, depending on the concentration of the individual distinct glycerol phases, but instead was determined by the total glycerol concentration in the silicone elastomer matrix. Surprisingly, there appears to be a synergetic contribution to the release kinetics from having two distinct glycerol phases on hydroquinone, as this active substance only showed near-zero order release kinetics without an initial burst at 80 phr total glycerol concentration, but in combination with erythrosine B showed zero-order release kinetics already at 80 phr total glycerol concentration in the silicone elastomer matrix.

Figure 12:
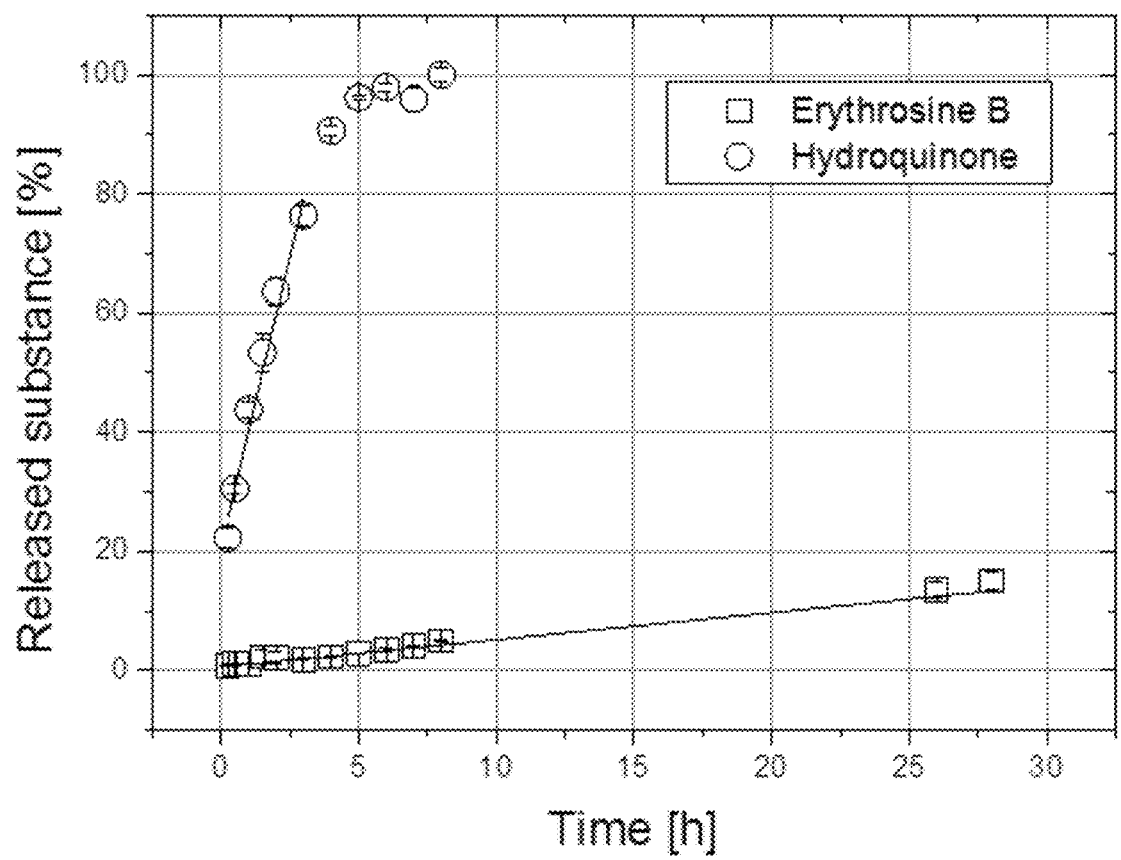
FIG. 12: Erythrosine B and hydroquinone release profiles from 0.3 mm thick dual compartment glycerol-silicone elastomers.
Figure 13:
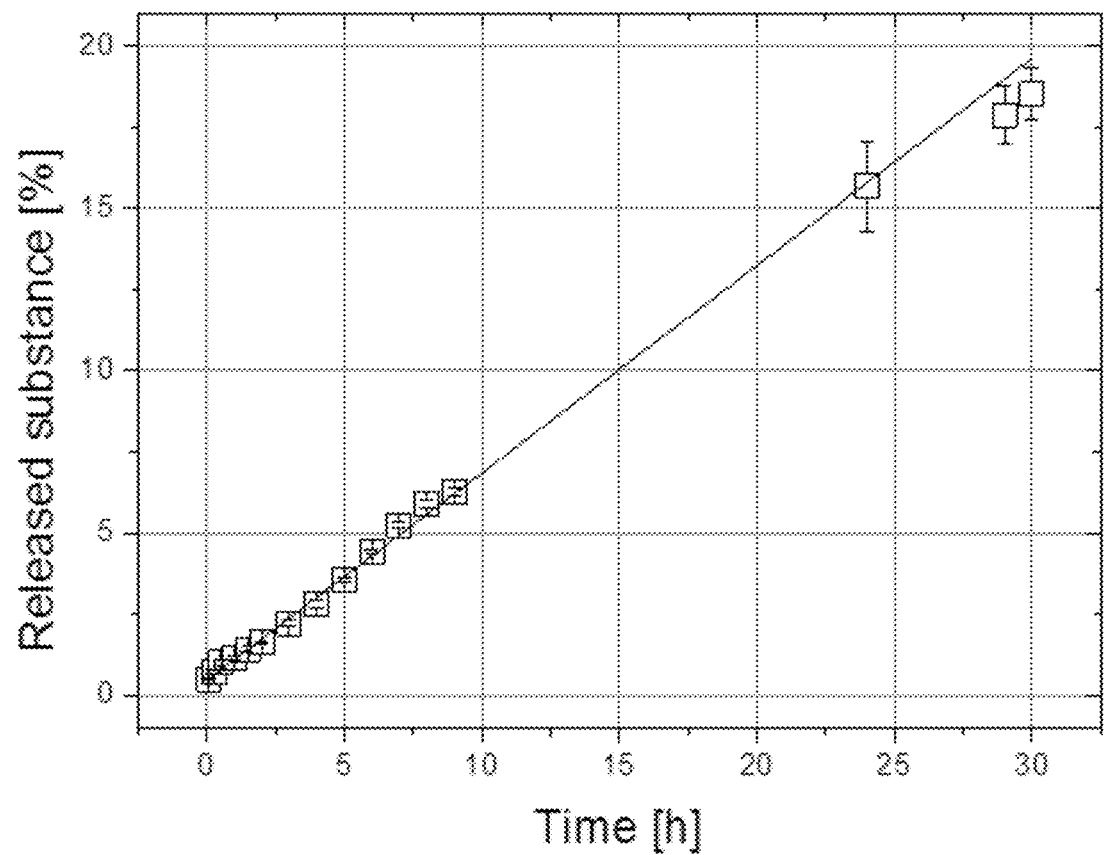
FIG. 13: Erythrosine B release profile from 0.3 mm thick glycerol-silicone elastomers.

The release behavior presented in FIG. 12 suggests that the two compounds are released with significantly different release rates from the glycerol-silicone elastomeric matrix. FIG. 13 discloses the release rate of erythrosine B from the same matrix without hydroquinone for comparison. The entire amount of incorporated hydroquinone was released after around 6 hours whereas only 15% of erythrosine B was released after 28 hours. Erythrosine B is a much larger molecule (higher molar volume) with a much more complex structure therefore such a diffusion behavior was expected. The results also prove that the zero-order release can be expected from the multiple compartment glycerol-silicone elastomers. Hydroquinone was released with the zero-order kinetics almost up to 80% of the total amount whereas erythrosine B was released with zero-order kinetics throughout the whole experiment (28 hours). Of particular interest, no initial active substance burst-effect was observed.

Example 4: Test of Various Silicone Pre-Elastomers for Use With the Compositions of the Invention The formation of stable glycerol-in-silicone emulsions was examined for a range of commercially available silicone pre-elastomers according to Table 2: Test of formation of compositions according to the invention and of maximum glycerol loading for various as received commercial silicone pre-elastomers. The test focused on maximum glycerol loading of the as received compositions and conditions for improving loading or stabilization of the as received compositions with glycerol.

The commercially available silicone pre-elastomers were used as received from the manufacturers. Curing was performed in accordance with the manufactures instructions.

In the experiments it was observed that the formation of stable glycerol-in-silicone emulsions was difficult when using Sylgard 186 (Dow Corning), Elastosil M4511 and M4514 (Wacker Chemie) due to very high viscosities of the compositions. The addition of viscosity modifying excipients, whereby the viscosities were reduced, allowed for the addition of glycerol. Silicone surfactants like Dow Corning FZ-2233 or Dow Corning ES-5300 were found particularly useful.

Additionally, various custom made hydrosilylation (materials from Gelest) and condensation (materials from Sika) cure compositions were designed and investigated. The materials from Gelest did not form stable emulsions unless fumed silica (even 3-5 phr) was incorporated. Only one custom condensation cure composition (Sika) was prepared. It allowed for introducing 80 phr of glycerol without using any filler.

In the experiments it was found that the presence of fumed silica has a strong influence on the stability of the glycerol-in-silicone emulsions for most silicone compositions, wherein as little as few phr of fumed silica efficiently stabilized the emulsions. Nevertheless, some silicone surfactants like Dow Corning FZ-2233 or Dow Corning ES-5300 enabled the formation of stable glycerol-in-silicone emulsions in silica-free systems Accordingly, in preferred embodiments of the invention, the compositions of the invention comprise fumed silica in an amount of between from 0.5 to 5 phr, between from 1 to 4 phr, between from 1.5 to 3 phr, or between from 2 to 2.5 phr.

CLOSING COMMENTS

The term "comprising" as used in the claims does not exclude other elements or steps. The term "a" or "an" as used in the claims does not exclude a plurality. Although the present invention has been described in detail for purpose of illustration, it is understood that such detail is solely for that purpose, and variations can be made therein by those skilled in the art without departing from the scope of the invention.

REFERENCES (1) Jain, K. K. *Drug Delivery Systems*; Humana Press: Basel, 2008.
(2) Peppas, N. A.; Khare, A. R. Preparation, Structure and Diffusional Behavior of Hydrogels in Controlled Release. Adv. Drug Deliv. Rev. 1993, 11, 1-35.
(3) Varelas, C. G.; Dixon, D. G.; Steiner, C. A. Zero-Order Release from Biphasic Polymer. Hydrogels. J. Control. Release 1995, 34 (3 SRC-GoogleScholar FG-1), 185-192.
(4) Bezemer, J. M.; Radersma, R.; Grijpma, D. W.; Dijkstra, P. J.; Feijen, J.; Van Blitterswijk, C. A. Zero-Order Release of Lysozyme from Poly(ethylene glycol)/Poly (butylene terephthalate) Matrices. J. Control. Release 2000, 64, 179-192.
(5) Feldstein, M. M.; Tohmakhchi, V. N.; Malkhazov, L. B.; Vasiliev, A. E.; Platé, N. A. Hydrophilic Polymeric Matrices for Enhanced Transdermal Drug Delivery. Int. J. Pharm. 1996, 131, 229-242.
(6) Jabbari, E.; Khakpour, M. Morphology of and Release Behavior from Porous Polyurethane Microspheres. Biomaterials 2000, 21, 2073-2079.
(7) Liu, H.; Farrell, S.; Uhrich, K. Drug Release Characteristics of Unimolecular Polymeric Micelles. J. Control. Release 2000, 68, 167-174.
(8) Matson, J. B.; Newcomb, C. J.; Bitton, R.; Stupp, S. I. Nanostructure-Templated Control of Drug Release from Peptide Amphiphile Nanofiber Gels. Soft Matter 2012, 8, 3586-3595.
(9) Guiseppi-Elie, A.; Brahim, S. I.; Recent, D. N. A Chemically Synthesized Artificial Pancreas: Adv. Mater. 2002, 14, 743-746.
(10) Fine, D.; Grattoni, A.; Hosali, S.; Ziemys, A.; De Rosa, E.; Gill, J.; Medema, R.; Hudson, L.; Kojic, M.; Milosevic, M.; Brousseau, L.; Goodall, R.; Ferrari, M.; Liu, X. A Robust Nanofluidic Membrane with Tunable Zero-Order Release for Implantable Dose Specific Drug Delivery. Lab Chip 2010, 10, 3074-3083.
(11) Woolfson, A. D.; Malcolm, R. K.; Gallagher, R. J. Design of a Silicone Reservoir Intravaginal Ring for the Delivery of Oxybutynin. J. Control. Release 2003, 91, 465-476.
(12) Malcolm, R. K.; McCullagh, S. D.; Woolfson, A. D.; Gorman, S. P.; Jones, D. S.; Cuddy, J. Controlled Release of a Model Antibacterial Drug from a Novel Self-Lubricating Silicone Biomaterial. J. Control. Release 2004, 97, 313-320.
(13) Murphy, P. S.; Evans, G. R. D. Advances in Wound Healing: A Review of Current Wound Healing Products. Plast. Surg. Int. 2012, 2012, 1-8.
(14) Silva, C. L.; Pereira, J. C.; Ramalho, A.; Pais, A. A. C. C.; Sousa, J. J. S. Films Based on Chitosan Polyelectrolyte Complexes for Skin Drug Delivery: Development and Characterization. J. Memb. Sci. 2008, 320, 268-279.
(15) Platt, A. J.; Phipps, A.; Judkins, K. A Comparative Study of Silicone Net Dressing and Paraffin Gauze Dressing in Skin-Grafted Sites. Burns 1996, 22, 543-545.
(16) Brook, M. A. Silicon in Organic, Organometallic, and Polymer Chemistry; John Wiley & Sons Inc.: Ontario, 2000.
(17) Mojsiewicz-Pieńkowska, K.; Jamrógiewicz, M.; Zebrowska, M.; Mikolaszek, B.; Sznitowska, M. Double Layer Adhesive Silicone Dressing as a Potential Dermal Drug Delivery Film in Scar Treatment. Int. J. Pharm. 2015, 481, 18-26.
(18) Mazurek, P.; Hvilsted, S.; Skov, A. L. Green Silicone Elastomer Obtained from a Counterintuitively Stable Mixture of Glycerol and PDMS. Polymer 2016, 87, 1-7.

(19) Mazurek, P.; Yu, L.; Gerhard, R.; Wirges, W.; Skov, A. L. Glycerol as High-Permittivity Liquid Filler in Dielectric Silicone Elastomers. J. Appl. Polym. Sci., 2016, 133, 1-8.
(20) Lee, J. N.; Park, C.; Whitesides, G. M. Solvent Compatibility of Poly(dimethylsiloxane)-Based Microfluidic Devices. Anal. Chem. 2003, 75, 6544-6554.
(21) Larsen, A. L.; Hansen, K.; Sommer-Larsen, P.; Hassager, O.; Bach, A.; Ndoni, S.; Jørgensen, M. Elastic Properties of Nonstoichiometric Reacted PDMS Networks. Macromolecules 2003, 36, 10063-10070.
(22) Michalak, I.; Mucha, M. The Release of Active Substances from Selected Carbohydrate Biopolymer Membranes. Carbohydr. Polym., 2012, 87, 2432-2438.
(23) Gokhale, A. Achieving Zero-Order Release Kinetics Using Multi-Step Diffusion-Based Drug Delivery. PharmTech 2014, 38, 1-3.
(24) Liechty, W. B.; Kryscio, D. R.; Slaughter, B. V.; Peppas, N. A. Polymers for Drug Delivery Systems. Annu. Rev. Chem. Biomol. Eng. 2010, 1, 149-173.
(25) Mazurek, P.; Brook, M.A.; Skov, A. L. Glycerol-Silicone Elastomers as Active Matrices with Controllable Release Profiles. Langmuir 2018, 34, 11559-11566.

The invention claimed is:

1. An elastomeric silicone composition comprising:
   a cured silicone elastomer matrix comprising a first glycerol phase and a second glycerol phase, which are distinct and separated by silicone wherein:
   (a) said first glycerol phase comprises a first active substance or drug and said second glycerol phase comprises a second active substance or drug;
   (b) said first active substance or drug being different than said second active substance or drug; and
   (c) wherein the first glycerol phase and the second glycerol phase are homogenously distributed in the cured silicone elastomer matrix; wherein said elastomeric silicone composition is incorporated into a transdermal patch.

2. The elastomeric silicone composition according to claim 1, wherein said first and said second active substance or drug are respectively hydroquinone and erythrosine B.

3. The elastomeric silicone composition according to claim 1, wherein said elastomeric silicone composition is made by:
   a) providing a first silicone composition comprising a first glycerol phase and a second silicone composition comprising a second glycerol phase;
   b) mixing said first and second silicone compositions at a shear level below 1000 rpm; and
   c) curing the mixed silicone composition obtained in b).

4. The elastomeric silicone composition according to claim 1, in the form of an emulsion or in the form of a cured elastomer.

* * * * *